United States Patent
Smith et al.

(10) Patent No.: US 9,487,750 B2
(45) Date of Patent: *Nov. 8, 2016

(54) METHODS AND COMPOSITIONS FOR GROWTH OF CELLS AND EMBRYONIC TISSUE ON A SYNTHETIC POLYMER MATRIX

(71) Applicant: The Regents of the University of Michigan, Ann Arbor, MI (US)

(72) Inventors: Gary D. Smith, Ann Arbor, MI (US); Joerg Lahann, Ann Arbor, MI (US); Himabindu Nandivada, Ann Arbor, MI (US); Thomas Eyster, Ann Arbor, MI (US); Luis Villa Diaz, Dearborn, MI (US); Paul Krebsbach, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 205 days.

This patent is subject to a terminal disclaimer.

(21) Appl. No.: 14/285,259

(22) Filed: May 22, 2014

(65) Prior Publication Data
US 2014/0255861 A1 Sep. 11, 2014

Related U.S. Application Data

(63) Continuation-in-part of application No. 13/726,918, filed on Dec. 26, 2012, now abandoned, which is a continuation of application No. 12/843,468, filed on Jul. 26, 2010, now abandoned, which is a continuation-in-part of application No. 12/530,126, filed as application No. PCT/US2008/056252 on Mar. 7, 2008, now Pat. No. 9,068,163.

(60) Provisional application No. 60/906,012, filed on Mar. 9, 2007.

(51) Int. Cl.
| | |
|---|---|
| C12N 5/0735 | (2010.01) |
| C12N 5/00 | (2006.01) |
| C08F 220/20 | (2006.01) |
| C08F 220/38 | (2006.01) |
| C08F 220/60 | (2006.01) |

(52) U.S. Cl.
CPC ........... *C12N 5/0606* (2013.01); *C12N 5/0068* (2013.01); *C08F 220/20* (2013.01); *C08F 220/38* (2013.01); *C08F 2220/606* (2013.01); *C12N 2533/30* (2013.01); *C12N 2533/40* (2013.01)

(58) Field of Classification Search
CPC .............. C12N 5/0606; C12N 5/0068; C12N 2533/30; C12N 2533/40; C12N 5/0735; C08F 220/20; C08F 220/38; C08F 2220/0606
See application file for complete search history.

(56) References Cited

U.S. PATENT DOCUMENTS

| 5,906,934 A | 5/1999 | Grande et al. |
| 2010/0068810 A1 | 3/2010 | Smith et al. |
| 2011/0033928 A1 | 2/2011 | Smith et al. |
| 2013/0102023 A1 | 4/2013 | Smith et al. |

OTHER PUBLICATIONS

Villa-Diaz et al., Nature Biotechnology, 28(6): 581-583, Jun. 2010.*
Nandivada, 2009, Development of Biomimetic Interfaces and Their Applications. Retrieved from University of Michigan Library. http://hdl.handle.net/2027.42/64816.*
Amit et al., "Feeder layer- and serum-free culture of human embryonic stem cells" 2004 Biol. Repro. 70:837-845.
Amit et al., "Human feeder layers for human embryonic stem cells" 2003 Biol. Repro. 68:2150-2156.
Anderson et al., 2004, "Nanoliter-scale synthesis of arrayed biomaterials and application to human embryonic stem cells", Nature Biotechnology 22:863.
Arasawa et al., "Grafting of zwitterion-type polymers onto silica gel surface and their properties" 2004 Reactive and Function Polymers 61: 153.
Azzaroni et al., "UCST wetting transitions of polyzwitterionic brushes driven by self-association" 2006 Angewandte Chemie, International Edition 45, 1770-1774.
Beattie et al., "Activin A maintains pluripotency of human embryonic stem cells in the absence of feeder layers" 2005 Stem Cells 23:489-495.
Brimble et al., "Karyotypic stability, genotyping, differentiation, feeder-free maintenance, and gene expression sampling in three human embryonic stem cell lines derived prior to Aug. 9, 2001" 2004 Stem Cells 13:585-597.
Cheon et al., "Defined feeder-free culture system of human embryonic stem cells" 2006 Biol. Reprod. 74:611 This reference was officially retracted by the authors.
Cho et al., "Highly efficient non-biofouling coating of zwitterionic polymers: poly((3-(methacryloylamino)propyl)-dimethyl(3-sulfopropyl)ammonium hydroxide)" 2007 Langmuir 23, 5678-5682.
Draper et al., "Recurrent gain of chromosomes 17q and 12 in cultured human embryonic stem cells" 2004 Nat. Biotech. 22:53-54.
Draper et al., 2004, "Culture and characterization of human embryonic stem cells", Stem Cells Devel. 13:325-336.
Ellerstrom et al., "Derivation of a xeno-free human embryonic stem cell line" 2006 Stem Cells 24:2170-2176.
Harris et al., "Zwitterions: Proof of the zwitterion constitution of the amino-acid molecule. II. Amino-acids, polypeptides, etc., and proteins as zwitterions, with instances of non-zwitterion ampholytes" 1930 Biochemical J. 24:1080.
Ilic, 2006, "Culture of human embryonic stem cells and the extracellular matrix microenvironment", Regenerative Medicine 1:95.
Imreh et al., "In vitro culture conditions favoring selection of chromosomal abnormalities in human ES cells" 2006 J. Cell Biochem. 99:508-516.

(Continued)

*Primary Examiner* — Thainan N Ton
(74) *Attorney, Agent, or Firm* — Casimir Jones, S.C.; Jason R. Bond

(57) ABSTRACT

The present invention provides methods and compositions for establishing and maintaining growth of cells and embryonic tissue on a synthetic polymer matrix. For example, the present invention provides synthetic growth matrices for stem cells, gametes, mature differentiated cells, and embryonic tissue (e.g., blastomeres, embryos, and embryoid bodies). In certain embodiments, the cells are capable of going through multiple passages while remaining in an undifferentiated state as a result of the synthetic polymer matrix.

2 Claims, 10 Drawing Sheets

(56) References Cited

OTHER PUBLICATIONS

Jiang et al., "Platelet adhesive resistance of polyurethane surface grafted with zwitterions of sulfobetaine" 2004 Colloids Surf B Biointerfaces 36, 19-26.
Klimanskaya et al., "Human embryonic stem cells derived without feeder cells" 2005 Lancet 365:1636-1641.
Li et al., "Hydrogels as Artificial Matrices for Human Embryonic Stem Cell Self-Renewal" 2006 J. Biomed. Mater. Res. vol. 79A pp. 1-5 "A".
Longo et al., "The chromosome make-up of mouse embryonic stem cells is predictive of somatic and germ cell chimaerism" 1997 Transgenic Res. 6:321-328.
Maitra et al., "Genomic alterations in cultured human embryonic stem cells" 2005 Nat. Genet. 37:1099-1103.
Mallon et al., "Toward xeno-free culture of human embryonic stem cells" 2006 Int. J. Biochem. Cell Biol. 38:1063-1075.
Matsubara et al., "A New Technique to Expand Human Mesenchymal Stem Cells Using Basement Membrane Extracellular Matrix." 2004 Biochem. Biophys. Res. Comm. vol. 313 pp. 503-508.
Mwale et al., "Suppression of Genes Related to Hypertrophy and Osteogenesis in Committed Human Mesenchymal Stem Cells Cultures on Novel Nitrogen-Rich Plasma Polymer Coatings." 2006 Tissue Engineering vol. 12 No. 9 pp. 2639-2647.
Skottman et al., "Culture conditions for human embryonic stem cells" 2006 Reproduction 132:691-698.
Stojkovic et al., "An autogeneic feeder cell system that efficiently supports growth of undifferentiated human embryonic stem cells" 2005 Stem Cells 23:306-314.
Thomson et al., "Embryonic stem cell lines derived from human blastocysts" 1998 Science 282:1145-1147.
Ullmann et al., "Epithelial-mesenchymal transition process in human embryonic stem cells cultured in feeder-free conditions" 2007 Mol. Human. Repro. 13:21-32.
Ware et al., "Controlled-rate freezing of human ES cells" 2005 Biotechniques 38:879-884.
Xu et al., "Feeder-free growth of undifferentiated human embryonic stem cells" 2001 Nat. Biotechnol 19:971-974.
Yuan et al., "Polyurethane vascular catheter surface grafted with zwitterionic sulfobetaine monomer activated by ozone" 2004 Colloids Surf B Biointerfaces 35, 1-5.
Zhao et al. 2000 Progress in Polymer Sci 25:677.
Brevini et al., "No Shortcuts to Pig Embryonic Stem Cells," Theriogenology, 2010, 71:544-550.
Cao et al., "Isolation and Culture of Primary Bovine Embryonic Stem Cell Colonies by a Novel Method," J Exp Zoo., 2009, 311A:368-376.
Konno et al., "Culture of Mouse Embryonic Stem Cells on Photoimmobilized Polymers," J Biosci Bioeng, 2006, 102(4):304-310.
Lim and Bodnar, "Proteome Analysis of Conditioned Medium from Mouse Embryonic Fibroblast Feeder Layers which Support the Growth of Human Embryonic Stem Cells," Proteomics, 2002, 2:1187-1203.
NIH, "Stem Cells: Scientific Progress and Future Research Directions," Dept. Health and Human Services, Chapter 1, pp. 1-4, Jun. 2001.
Paris and Stout, "Equine Embryos and Embryonic Stem Cells: Defining Reliable Markers of Pluripotency," Theriogenology, 2010, 74:516-524.
Prowse et al., "A Proteome Analysis of Conditioned Media from Human Neonatal Fibroblasts Used in the Maintenance of Human Embryonic Stem Cells," Proteomics, 2005, 5:978-989.
Thomson et al., "Isolation of a Primate Embryonic Stem Cell Line," PNAS, 1995, 92:7844-7848.
Takashi et al., "induction of Pluripotent Stem Cells from Adult Human Fibroblasts by Define Factors," Cell, 2007, 131: (5): 861-72.
Ludwig et al., "Derivation of human embryonic stem cells in defined conditions," Nat Biotech., 2006, 24:185-187.
Jing et al., "Hematopoietic stem cells in co-coulture with mesenchymal stromal cells—modeling the niche compartments in vitro," Haematologica, 2010, 95(4):542-550.
Sigma-Aldrich catalog. http://www.sigmaaldrich.com/catalog/, accessed online on Jun. 4, 2010, "neural stem cells" and "Stemline Neural Stem cell Expansion Medium,".

\* cited by examiner

Propyl dimethyl (3-sulfopropyl) ammonium hydroxide

Propyl dimethyl (3-sulfoakyl) ammonium hydroxide (GENERALIZED)

3-(methacryloylamino) propyl dimethyl (3-sulfopropyl) ammonium hydroxide 3-(methacryloylamino) propyl dimethyl (3-sulfoalkyl) ammonium hydroxide (GENARALIZED)

2-(methacryloyloxy) ethyl dimethyl (3-sulfopropyl) ammonium hydroxide 2-(methacryloyloxy) ethyl dimethyl (3-sulfoalkyl) ammonium hydroxide
(GENERALIZED)

2-(methacryloyloxy)ethyl dimethyl(3-phosphonylpropyl)ammonium

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ctgcagtgtg ggtttcgggc a                                            21

<210> SEQ ID NO 2
```

<211> LENGTH: 24
<212> TYPE: DNA
<213> ORGANISM: Artificial Sequence
<220> FEATURE:
<223> OTHER INFORMATION: Synthetic

<400> SEQUENCE: 2
cttgctgcag aagtgggtgg agga                                    24

<210> SEQ ID NO 3
<211> LENGTH: 16
<212> TYPE: DNA
<213> ORGANISM: Artificial Sequence
<220> FEATURE:
<223> OTHER INFORMATION: Synthetic

<400> SEQUENCE: 3
atgcaccgct acgacg                                             16

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cttttgcacc cctcccattt                                         20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ctccttcagg cagtgagagc                                         20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gagatgcagt gtgctcgtgc                                         20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgagcctttc cagcaagttt                                         20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cttccccgtc tcaggtatca                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tctgtggaga acgacatcca                                              20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
ctgtacgtct cagctctgtg a                                            21

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
atctggcacc acaccttcta caatgagctg cg                                32

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
cgtcatactc ctgcttgctg atccacatct gc                                32

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
cggcttcctc ctcttcctct atac                                         24

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
atcgatttca ctcatcttca cacgtc                                       26

<210> SEQ ID NO 15
<211> LENGTH: 20
<212> TYPE: DNA

```
<213> ORGANISM: Artificial Sequence
<220> FEATURE:
<223> OTHER INFORMATION: Synthetic

<400> SEQUENCE: 15
cggaagagtg tctggagcaa                                                  20

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
ggatgaagcg gagtctgga                                                   19

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
cagctggcgc acctcaagat g                                                21

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
agggaagttg ggctcaggac tgg                                              23

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
acgggatgac caagtacagc                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
acacactttg ggctggtagg                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
atcagagatc aggaagcacc                                                  20
```

-continued

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ggaacttcat ctgggtccat                                          20

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
ccatgtacat gagcactgtt g                                        21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
ctccaataac tcctggtatc c                                        21

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
gagagaaaga aagggagaga ag                                       22

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gagagaggca aactggaatc                                          20

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
tcctcctctt cctctatact aac                                      23

<210> SEQ ID NO 28
<211> LENGTH: 18
<212> TYPE: DNA
<213> ORGANISM: Artificial Sequence
<220> FEATURE:

```
<223> OTHER INFORMATION: Synthetic

<400> SEQUENCE: 28
cccacaaatc aggcatag                                                   18

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
agtcagtgaa cagggaatgg                                                 20

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
tcgggattca agaacctcg                                                  19

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
gccgaggact ttgattgc                                                   18

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
gtgtggactt gggagagg                                                   18
```

METHODS AND COMPOSITIONS FOR GROWTH OF CELLS AND EMBRYONIC TISSUE ON A SYNTHETIC POLYMER MATRIX

The present application is a continuation-in-part of U.S. application Ser. No. 13/726,918, filed Dec. 26, 2012, which is a continuation-in-part of U.S. application Ser. No. 12/530,126, filed Nov. 30, 2009, which is a U.S. National Entry of International Application No. PCT/US08/56252, filed Mar. 7, 2008, which in turn claims priority to U.S. Provisional Application 60/906,012, filed Mar. 9, 2007, all of which are herein incorporated by reference in their entireties.

This invention was made with government support under GM069985 awarded by the National Institute of Health. The government has certain rights in the invention.

FIELD OF THE INVENTION

The present invention provides methods and compositions for establishing and maintaining growth of cells and embryonic tissue on a synthetic polymer matrix. For example, the present invention provides synthetic growth matrices for stem cells, gametes, mature differentiated cells, and embryonic tissue (e.g., blastomeres, embryos, and embryoid bodies). In certain embodiments, the cells are capable of going through multiple passages while remaining in an undifferentiated state as a result of the synthetic polymer matrix.

BACKGROUND OF THE INVENTION

Human and other mammalian stem cells including embryonic stem cells (hESCs and ESCs), which are pluripotent cells derived from pre-implantation embryos, have enormous potential as predicative models of early development or for cell replacement therapies (Draper et al., 2004, Stem Cells & Devel. 13:325-336). Because hESCs show remarkable sensitivity towards environmental influences, their continuous undifferentiated growth has been a major challenge undermining widespread use of hESCs in many applications. Currently, sustained hESC cultures still require naturally-derived cell substrates, such as mouse or human embryonic fibroblast cells, MATRIGEL, laminin, or fibronectin (Draper et al. 2004; Stojkovic et al., 2005, Stem Cells 23:306-314; Xu et al., 2001, Nat. Biotech. 19:971-974; Mallon et al., 2006, Int. J. Biochem. Cell Biol. 38:1063-1075; Amit et al., 2004, Biol. Repro. 70:837-845; Amit et al., 2003, Biol. Repro. 68:2150-2156; Skottman et al., 2006, Reproduction 132:691-698; Thomson et al., Science 282:1145-1147; Ellerstrom et al., 2006, Stem Cells 24:2170-2176; Xu et al., 2001, Nat. Biotechnol 19:971-974; Cheon et al., 2006, Biol. Reprod. 74:611; Beattie et al., 2005, Stem Cells 23:489-495).

However, xenogenic culture matrices are associated with several shortcomings. While co-culture systems with fibroblasts complicate direct studies of self-renewal and/or differentiation mechanisms of hESCs, cell substrates based on MATRIGEL and other naturally derived matrices show batch-to-batch inconstancies and may be prone to contaminations. To address these challenges, synthetic polymers have been proposed as cell culture substrates of hESC, because of their well-defined and reproducible fabrication, but have not yet been established for long-term hESC cultures.

As such, what are needed are compositions and methods that provide an environment for growth and maintenance of embryonic stem cells. The establishment of defined microenvironments for stem cell culture addresses a major issue of human embryonic stem cell research, and will provide embryonic stem cells useful in, for example, research purposes and potential clinical treatments of diseases.

SUMMARY OF THE INVENTION

The present invention provides methods and compositions for establishing and maintaining growth of cells and embryonic tissue on a synthetic polymer matrix. For example, the present invention provides synthetic growth matrices for stem cells, gametes, mature differentiated cells, and embryonic tissue (e.g., blastomeres, embryos, and embryoid bodies). In certain embodiments, the cells are capable of going through multiple passages while remaining in an undifferentiated state as a result of the synthetic polymer matrix.

Certain illustrative embodiments of the invention are described below. The present invention is not limited to these embodiments.

In some embodiments, the present invention provides compositions for growth and maintenance of cells or embryonic tissue comprising: a synthetic polymer matrix and a culture medium, wherein the synthetic polymer matrix is selected from the group consisting of: i) a first polymer which comprises a zwitterionic group; ii) a co-polymer comprising poly[2-(methacryloyloxy)ethyl dimethyl-(3-sulfopropyl)ammonium hydroxide] (PMEDSAH) and poly(ethylene glycol methacrylate) (PPEGMA); iii) a copolymer comprising PMEDSAH and poly(2-(methacryloyloxy)ethyl)trimethylammonium chloride (PMETAC); and iv) a copolymer comprising 2-hydroxyethyl methacrylate (HEMA) and PMEDSAH.

In certain embodiments, the zwitterionic group of the first polymer is

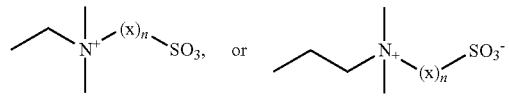

where x is selected from the group consisting of any aliphatic or substituted aliphatic chain, any aryl or substituted chain, hydrogen, or a combination thereof; and n is an integer of 1 or greater. In further embodiments, the first polymer comprises a polymer of the following structure:

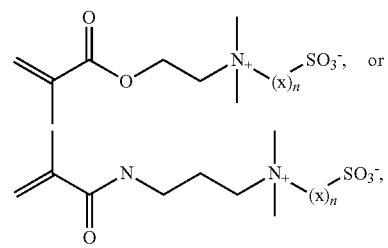

where x is selected from the group consisting of any aliphatic or substituted aliphatic chain, any aryl or substituted chain, hydrogen, or a combination thereof; and n is an integer of 1 or greater. In particular embodiments, the first polymer comprises either zwitterionic group is poly[2-

(methacryloyloxy)ethyl dimethyl(3-sulfopropyl)ammonium] (PMEDSA) or Poly[[3-(methacryloylamino)propyl] dimethyl(3-sulfopropyl)ammonium hydroxide] (PMAPDSAH).

In particular embodiments, the zwitterionic group of the first polymer comprises a zwitterionic phosphonate group. In other embodiments, the zwitterionic group of the first polymer comprises a zwitterionic phosphate group. In further embodiments, the zwitterionic group of the first polymer comprises a moiety with the following structure:

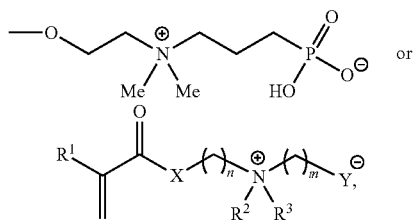

wherein R1, R2, and R3 are the same or different alkyl groups; wherein X is O, NH, or NR4 (e.g., wherein R4 is an alkyl group or any other type of organic moiety); and wherein Y is a sulfonate, a phosphonate, or a phosphate.

In further embodiments, the synthetic polymer matrix has a thickness of between 5 nm and 500 nm, between 10 nm and 200 nm, between 20 and 150 nm, or 90-120 nm (e.g., about 5 nm . . . 20 nm . . . 50 nm . . . 75 nm . . . 95 nm . . . 105 nm . . . 110 nm . . . 115 nm . . . 130 nm . . . 145 nm . . . 200 nm . . . 500 nm). In other embodiments, the synthetic polymer matrix is synthesized by atom transfer radical polymerization (ATRP). In certain embodiments, the synthetic polymer matrix has a top surface, and wherein the top surface has a contact angle between 1 and 70 degrees, between 5 and 60 degrees, or between 15 and 45 degrees (e.g., about 1 . . . 5 . . . 15 . . . 25 . . . 38 . . . 49 . . . 58 . . . 64 . . . and 70 degrees).

In some embodiments, the cells are stem cells, and wherein the stem cells remain pluripotent and maintain native karyotype after at least 5 passages (e.g., at least 5 . . . 10 . . . 15 . . . 20 . . . 25 . . . 30 or more). In further embodiments, the compositions further comprise cells or embryonic tissue selected from the group consisting of: adult stem cells, embryonic stem cells, mature male gametes, mature female gametes, immature male gametes, immature female gametes, parthenotes, embryos, embryos derived from somatic cell nuclear transfer, individual undifferentiated blastomeres, small clusters of undifferentiated blastomeres, individual early differentiated blastomeres, small clusters of early differentiated blastomeres, conventional embryonic stem (ES) cells derived from inner cell mass of pre-implantation embryos, conventional embryonic stem (ES) cells derived for inner cell mass of post-implantation stage embryos, genetically abnormal ES cells, genetically altered ES cells, trophoblast outgrowth, embryoid bodies, adult or germline stem cells, committed progenitor cells, neural progenitor cells, hematopoietic stem cells, mesenchymal stem cells, mammary stem cells, cancer stem cells, cord blood stem cells, amniotic cells, induced pluripotent stem (iPS) cells derived from somatic cells, and mature differentiated cells.

In certain embodiments, the present invention provides methods for culturing cells or embryonic tissue comprising: a) applying cells to a substrate, wherein the substrate comprises a culture medium and a synthetic polymer matrix, wherein the synthetic polymer matrix is selected from the group consisting of: i) a first polymer which comprises a zwitterionic group; ii) a co-polymer of poly[2-(methacryloyloxy)ethyl dimethyl-(3-sulfopropyl)ammonium hydroxide] (PMEDSAH) and poly(ethylene glycol methacrylate) (PPEGMA); iii) a copolymer of PMEDSAH and poly(2-(methacryloyloxy)ethyl)trimethylammonium chloride (PMETAC); and iv) a copolymer of 2-hydroxyethyl methacrylate (HEMA) and PMEDSAH; and b) growing the cells or the embryonic tissue on the substrate.

In other embodiments, the zwitterionic group of the first polymer is

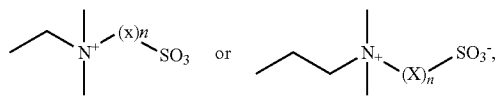

where x is selected from the group consisting of any aliphatic or substituted aliphatic chain, any aryl or substituted chain, hydrogen, or a combination thereof; and n is an integer of 1 or greater. In additional embodiments, the first polymer comprises poly[2-(methacryloyloxy)ethyl dimethyl (3-sulfopropyl)ammonium] (PMEDSAH) or Poly[[3-(methacryloylamino)propyl]dimethyl(3-sulfopropyl)ammonium hydroxide] (PMAPDSAH). In certain embodiment, the cells maintain pluripotency and native karyotype after at least 5 passages (e.g., at least 5 . . . 15 . . . 25 . . . 35 . . . or more).

In certain embodiments, the cells or embryonic tissue is selected from the group consisting of adult stem cells, embryonic stem cells, mature male gametes, mature female gametes, immature male gametes, immature female gametes, parthenotes, embryos, embryos derived from somatic cell nuclear transfer, individual undifferentiated blastomeres, small clusters of undifferentiated blastomeres, individual early differentiated blastomeres, small clusters of early differentiated blastomeres, conventional embryonic stem (ES) cells derived from inner cell mass of pre-implantation embryos, conventional embryonic stem (ES) cells derived for inner cell mass of post-implantation stage embryos, genetically abnormal ES cells, genetically altered ES cells, trophoblast outgrowth, embryoid bodies, adult or germline stem cells, committed progenitor cells, neural progenitor cells, hematopoietic stem cells, mesenchymal stem cells, mammary stem cells, cancer stem cells, cord blood stem cells, amniotic cells, induced pluripotent stem (iPS) cells derived from somatic cells, and mature differentiated cells.

In additional embodiments, the methods further comprise the step of differentiating the embryonic stem cells under conditions such that the embryonic stem cells form representative cells of embryonic germ cell layers. In further embodiments, the embryonic stem cells are human embryonic stem cells. In certain embodiments, the methods further comprise the step of exposing the cells or the embryonic tissue to a test compound. In additional embodiments, the test compound is a drug. In particular embodiments, the first polymer comprises a polymer of the following structure:

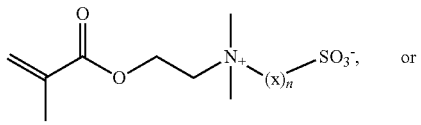

-continued

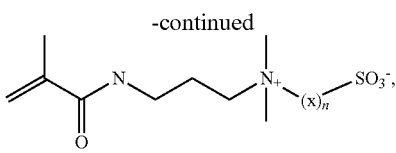

where x is selected from the group consisting of any aliphatic or substituted aliphatic chain, any aryl or substituted chain, hydrogen, or a combination thereof; and n is an integer of 1 or greater. In other embodiments, the embryonic tissue comprises an embryo.

In certain embodiments, the synthetic polymer matrixes of the present invention are employed for uses including, but not limited to, derivation of normal embryonic stem cells; differentiation of normal embryonic stem cells into different lineages; derivation of induced pluripotent stem (iPS) cells reprogrammed from somatic cells; culture of adult stem cells; stem cell culture in defined conditions for drug screening; derivation of genetically abnormal ES cells; differentiation of genetically abnormal embryonic stem cells into different lineages; derivation and differentiation of ES cells from individual or small clumps of undifferentiated blastomeres; derivation and differentiation of ES cells from individual or small clumps of early differentiated blastomeres; solid-state cell differentiation and organogenesis; growth and development of gametes in vitro; and embryo selection.

In some embodiments, the synthetic polymer matrix of the present invention comprises a co-polymer of MEDSAH with other methacrylated monomers selected from the group consisting of: 2-hydroxyethyl methacrylate (HEMA), poly(ethylene glycol)methyl ether methacrylate (PEGMA), carboxybetaine methacrylate (CBMA), (2-(methacryloyloxy)ethyl)trimethylammonium chloride (METAC), 3-sulfopropyl methacrylate (SPMA).

In one embodiment, the present invention provides artificial polymer matrices for use in cultures stem cells (e.g., embryonic stem cells (ESCs) or adult stem cells). In some embodiments, such matrices support ESC colony formation, proliferation and maintenance of a pluripotent state. In one embodiment, the artificial polymer matrices are comprised of synthetic hydrogels. In some embodiments, the present invention provides artificial polymer matrices fabricated without the addition of naturally derived biomolecules, such as extracellular matrix components, growth factors, laminin, matrigel, fibronection, vitronectin, collagen, gelatin, and so on. In some embodiments, the artificial polymer matrix comprises negatively charged groups, such as phosphate groups, sulfate groups, carboxyl groups, sulfonate groups, phosphonate groups, and the like. In some embodiments, the artificial polymer matrices may further comprise positively charged groups, such as ammonium groups, and the like. In some embodiments, the artificial polymer matrices comprise simultaneously positively and negatively charged groups. In some embodiments, the artificial polymer matrices comprise, at least in part, zwitterionic groups (e.g., sulfobetaine). For example, zwitterionic groups are combined with other charged groups, such as positively and/or negatively charged groups. The matrix may comprise one or more types of zwitterionic groups. The incorporation of zwitterionic groups into the artificial polymer matrices allows the materials to engage in strong inter- and intramolecular deipolar interactions which span from a non-associated to a fully associated regime, behavioral characteristic for zwitterionic molecules. In one embodiment of the present invention the artificial polymer matrices comprise one, or more than one, type of zwitterionic group. In some embodiments, the zwitterionic group is

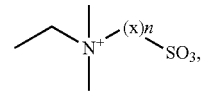

where x is any aliphatic or substituted aliphatic chain, aryl or substituted aryl chain, or hydrogen; and n is an integer of 1 or greater. In other embodiments the artificial polymer matrix comprises sulfobetaine groups. In certain embodiments, the present invention provides a synthetic cell matrix system comprising:

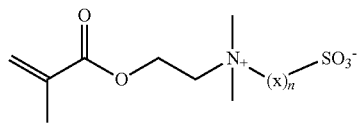

In some embodiments, the present invention provides a synthetic cell matrix system comprising, for example, poly[2-(methacryloyloxy)ethyl dimethyl(3-sulfopropyl)ammonium] (PMEDSAH) hydrogels or copolymers or blends thereof, or functional equivalents thereof, that supports long-term proliferation and passaging of hESCs. For example, during development of embodiments of the present invention, hESCs were subjected to at least eighteen continuous passages over a period of approximately seven months without undergoing unregulated differentiation. For example, hESCs cultured on PMEDSAH hydrogels retained normal karyotypes and continuously and consistently displayed the markers of undifferentiated hESCs. This is the first time that hESCs exhibited undifferentiated growth and passaging for extended times on fully synthetic cell matrices void of any xenogenic or previously used components.

In some embodiments, provided herein are compositions, kits, and systems comprising a synthetic polymer matrix, wherein said synthetic polymer matrix: i) comprises poly[2-(methacryloyloxy)ethyl dimethyl-(3-sulfopropyl)ammonium hydroxide] (PMEDSAH) (or one of the other polymers described herein), ii) has a thickness between 10 nm and 155 nm (e.g., about 10 nm . . . 30 nm . . . 55 nm . . . 85 nm . . . 100 nm . . . 105 nm . . . 125 nm . . . or 155 nm; or about 90 to 120 nm); and/or iii) has a top surface with a contact angle between 5 and 60 degrees (e.g., about 5 . . . 25 . . . 45 . . . or 60 degrees). In certain embodiments, the compositions, kits, or systems further comprise culture medium. In other embodiments, the compositions, kits, or systems further comprise cells (e.g., human embryonic stem cells or other stem cells). In some embodiments, the synthetic polymer matrix is generated by a method comprising atom transfer radical polymerization (ATRP) and has a thickness between 75 nm and 135. In further embodiments, provided herein are methods of culturing cells (e.g., hESCs) on with such compositions, kits, and systems. In one embodiment, the artificial polymers form, for example, a three-dimensional polymer matrix structure. In yet another embodiment, biomolecules are further immobilized into the artificial polymer matrix. In some embodiments, biomolecules include, but are not limited to, small molecules for cell based therapies and treatments, drug delivery, and the like. In some embodiments, such polymer matrix structures provide, for example, scaffolds for cell growth for tissue regeneration.

In one embodiment, the present invention provides for the use of a synthetic hydrogel matrix comprising glycoproteins in growing and maintaining stem cells (e.g., embryonic stem cells or adult stem cells) in a pluripotent state, with native karyotype, for multiple passages. In some embodiments, the present invention provides for methods of culturing stem cells comprising providing stem cells, applying the stem cells to a substrate that has been treated with a synthetic hydrogel as previously described, and growing the stem cells on the substrate such that their pluripotency and native karyotype is maintained. In some embodiments, culture methods further comprise the use of a fully defined media.

In some embodiments, the present invention provides for compositions and methods of culturing stem cells for use in drug screening. In some embodiments, the present invention provides compositions and methods for culturing stem cells for use in screening for modulators of stem cell differentiation. In some embodiments, the present invention provides compositions and methods for culturing stem cells for use in research applications. In some embodiments, the present invention provides compositions and methods for culturing stem cells for use in clinical applications, such as determining compositions, drugs, small molecules, useful for, for example modulating stem cells for subsequent use in transplantation or treatment of diseases (e.g., leukemia, liver disease, brain diseases, proliferative diseases, etc).

In some embodiments, the present invention provides for compositions and methods for culturing embryos using the substrates described herein and optionally culture media suitable for culture of embryos.

DESCRIPTION OF THE FIGURES

FIG. 10a shows photographs of stained cells, FIG. 10b shows the number of cells after 1 week, and FIG. 10c shows the number of cells after 5 weeks.

DEFINITIONS

Figure 1:
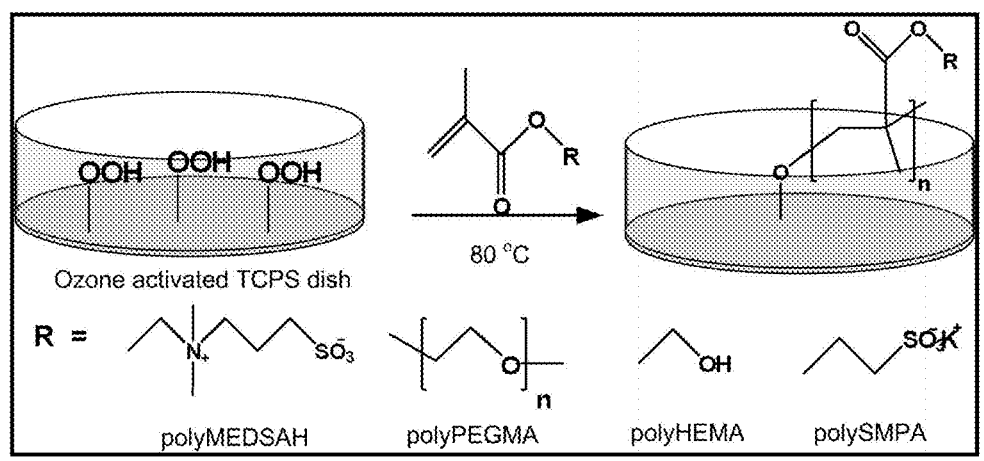
FIG. 1 shows exemplary compositions attached TCPS dishes, thereby creating substrates that are coated with different synthetic polymer matrices.

As used herein, the term "multiple passages", "multiple passaging", and/or "multiple mechanical passages or passaging", refers to the number of times a cell is grown in vitro on a tissue culture substrate, released from that substrate, and reapplied to another substrate. For example, the present invention described embodiments where human embryonic stem cells were passaged numerous, thereby demonstrating that cells can be applied to a substrate, released from a substrate, and reapplied to another substrate while still allowing for growth and maintenance of the cell culture.

As used herein, the term "substrate" refers to a surface for cell culture. A substrate can be, for example, a glass slide, a culture dish, culture plates, glass or composite beads, chip microchannels, and the like. The present invention is not limited by the type of substrate used.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, $—NH_2$, $—NHCOCH_3$, $—OH$, lower alkoxy ($C_1$-$C_4$), halo ($—F$, $—Cl$, $—Br$, or $—I$).

As used herein, the term "substituted aliphatic," refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "linker" refers to a chain containing up to and including eight contiguous atoms connecting two different structural moieties where such atoms are, for example, carbon, nitrogen, oxygen, or sulfur.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

Certain illustrative embodiments of the invention are described below. The present invention is not limited to these embodiments.

The chemistry and morphology of the microenvironment surrounding a human embryonic stem cell plays an important role in the cellular behavior, controlling the orchestration of various developmental events, such as cell proliferation, differentiation, migration, and apoptosis. Given the importance of the chemical signature of the microenvironment, the development of fully-defined synthetic matrices is an important step towards fully synthetic cell culture systems, but will largely depend on materials selection for the cell substrate. Several synthetic polymers, such as PLGA, PLA, and PNIPAM-based polymers, as well as polymers obtained using combinatorial methods, have been previously evaluated. While these studies contributed to a fundamental appreciation of the importance of the chemical identity of the microenvironment, they fall short in reporting long-term undifferentiated growth and passaging of hESCs.

In developing embodiments of the present invention, functionally diverse groups of synthetic hydrogels and their use in hESCs adhesion studies were identified, and their subtle interrelationships between synthetic polymer matrices and hESCs, for example, were examined. Four hydrogels comprising identical methacrylate backbone structures, but different side chain chemistries, were deposited onto the surface of tissue culture styrene (TCPS) dishes via surface-initiated graft-polymerization. The resulting synthetic polymers were hydrogels with high to moderate hydrophilicity. On the basis of their side chain chemistries, these materials are classified as hydrogen-bond acceptors (PHEMA), hydrogen-bond donors (PPEGMA), charge-donors (PSMPA), or polyzwitterions (e.g., PMEDSAH) (FIG. 1).

Artificial polymer matrices can be deposited onto the surface of a substrate, for example, using standard methods known to one skilled in the art. These methods may include surface physisorption or chemisorption. Physisorption includes, for example, the static and dynamic coating with polymers and/or oligomers. Chemisorption includes methods such as surface-initiated polymerization, grafting including grafting-from and grafting-to techniques, covalent tethering to the surface, crosslinking using exposure of the substrate to a solution of a polymer and/or oligomers followed by treatment with an energy source, such as plasma, UV, gamma radiation, ion beam, and the like.

Undifferentiated hESCs from cell lines H9 and BG01 growing on MEF as previously described (Thomson et al, 1998), were mechanically harvested and seeded onto the different hydrogel-coated plates. The surfaces were compared to solvent-casted poly(α-hydroxy esters), PLA, PLGA, and MATRIGEL coated substrates. Cell culture experiments were conducted in MEF-conditioned medium (MEF-CM) (Amit et al., 2003). Following initial hESC seeding, no cell attachment was observed on PLA, PLGA, the negatively charged PSPMA substrate, or PHEMA (Table 1).

TABLE 1

| Polymer | Contact angle | Attachment | Long term |
|---|---|---|---|
| polyMEDSA | 45 | + | + |
| polyHEMA | 55 | − | − |
| polyPEGMA | 60 | + | − |
| polySPMA | 80 | − | − |
| PLA | | − | − |
| PLGA | | − | − |

In contrast, hESC attachment was observed on poly(ethylene glycol)methyl ether methacrylate (PEGMA), and unmodified TCPS plates; however colonies did not grow with time and/or hESCs spontaneously differentiated during the first or second passage. These data are consistent with the recently reported short-term self-renewal of hESCs on polymer matrices (Li et al., 2006, J. Biomad. Mater. Res. A 79:1-5). None of the hydrogels showed consistent long-term growth, consecutive passaging, and maintenance of long-term pluripotency. MATRIGEL-coated dishes and PMEDSAH hydrogel coatings supported initial cell adhesion and proliferation.

The physical and chemical properties of PMEDSAH coatings were characterized using a combination of surface analytical tools including X-ray photoelectron microscopy (XPS), Fourier transform infrared spectroscopy (FT-IR), imaging ellipsometry, and scanning probe microscopy (SPM). PMEDSAH films used had an average surface root mean square roughness of 0.91 nm as determined by SPM. Imaging ellipsometry showed PMEDSAH film thicknesses between 10 and 2000 nm. The polymer films were stable when stored for extended times in aqueous solutions. As such, it was concluded that the PMEDSAH coatings were characterized by ultra-thin, smooth polymer films chemically tethered to the TCPS substrate. FT-IR spectra showed distinct bands at 1724 $cm^{-1}$ indicating the presence of carbonyl groups characteristic of PMEDSAH. To further confirm initial evidence from the FT-IR studies that indicated the presence of twitterionic groups on the surface, the elemental surface composition of PMEDSAH coatings was quantified by X-ray photoelectron spectroscopy (XPS). The presence of characteristic peaks associated with nitrogen, sulfur, and oxygen, and the relative composition of these elements correlated well with the expected chemical composition of PMEDSAH. In addition, the high resolution $C_{1s}$ spectrum of PEDMSAH revealed characteristic signals associated with hydrocarbon (C—H/C) peak at 285.0 eV, ammonium-bond carbon (—C—$N^+$($CH_3$)$_2$—) at 286.4 eV, and ester carbon (—COO—) peak at 288.9 eV. Taken together, FTIR and XPS analysis confirms the overall chemical composition of PMEDSAH coating, and demonstrates the presence of twitterionic groups at the surface of the coating. Moreover, contact angle measurements revealed an advancing contact angle of above 45 degrees of the PMEDSAH coating, which is in accordance with a self-associated super-coiled regime. It was determined, therefore, that the PMEDSAH coatings used in developing embodiments of the present invention, have, for example, properties that distinguish them from the other hydrogel coatings.

Initial experiments revealed, for example, a positive influence of PMEDSAH hydrogels on human embryonic cell culture adhesion and proliferation when compared to other synthetic polymers. In additional experimentation, growth and passaging of hESC on PMEDSAH and MATRIGEL dishes over a period of 6 months was performed. Human ESCs were passaged multiple times (e.g., for example, up to 18 passages; i.e., greater than 2, 5, 10, 15 passages) and cell fate of hESCs was continuously monitored by immunostaining. It was observed that PMEDSAH hydrogels supported cell attachment, colony growth, and hESC proliferation for more than eight months (e.g., more than 1, 2, 4, 6, months) over multiple passages. Human ESCs were characterized at regular intervals throughout the course of experimentation. After 7 months (roughly 18 passages), hESCs cultured on PMEDSAH expressed pluripotency markers, such as OCT3/4, SOX-2, SSEA-4, TRA-1-60 and TRA-1-81 (FIG. 2A), and retained normal karyotypes. The latter is an important aspect, for example, because the long-term culture of mouse (Longo et al., 1997, Transgenic Res. 6:321-328) and human (Draper et al., 2004, Nat. Biotech. 22:53-54; Maitra et al., 2005, Nat. Genet. 37:1099-1103) ESCs can lead to distinct chromosomal abnormalities and hESC feeder-free culture may bias for occurrence in aneuploidy (Matira et al., 2005; Brimble et al., 2004, Stem Cells 13:585-597). In concordance, chromosome instability and decreased pluripotency of hESCs was reported on cells adapted to grow on TCPS plates and passaged by enzymatic method (Imreh et al., 2006, J. Cell Biochem. 99:508-516).

Pluripotency of hESCs was tested in vitro by embryoid body (EB) formation and identification of genes representative of the three germ line cells: ectoderm (KRT-18), mesoderm (BMP-4) and endoderm (GATA-4) and several other cell-tissue specific genes (FIG. 2B). Occasionally, spontaneous differentiation of hESCs growing on PMEDSAH as well as MATRIGEL was observed at very low rates (<5%). The observed differentiated colonies can be divided into two groups; A) one subpopulation had indistinct borders, with larger cells that migrated away from the colony, and B) another subpopulation of fibroblast-like cells growing between undifferentiated hESC colonies. These fibroblast-like cells were negative for hESC markers. Similar fibroblast-like cells surrounding undifferentiated hESC colonies have been reported previously for feeder-free hESC cultures (Xu et al., 2001, Nat. Biotech. 971-974; Klimanskaya et al., 2005, Lancet 365:1636-1641; Ullmann et al., 2007, Mol. Human. Repro. 13:21-32).

As such, one embodiment the present invention provides synthetic glycoprotein coated substrates, for example PMEDSAH coated substrates, for culturing hESCs wherein the cultured hESCs maintain pluripotency and normal karyotypes. In some embodiments, the PMEDSAH coated surfaces support hESC culture and mechanical propagation for at least 3 passages, at least 5 passages, at least 7 passages, at least 10 passages, at least 15 passages, at least 18 passages over a period of, for example, at least 3 months, at least 5 months, at least 7 months while retaining normal hESC karyotype and pluripotency.

While performing experimentation in development of embodiments of the present invention, phenotypes and genotypes of hESCs cultured on PMEDSAH were basically undistinguishable from those cultured on MATRIGEL. However, interesting differences with respect to the proliferation kinetics were observed between hESCs grown on PMEDSAH and MATRIGEL. For example, while monitored the time between passages (e.g., the time that it takes for a cell population to obtain cell densities sufficient for passaging), colonies grown on PMEDSAH required approximately 17 days to reach their first passage point.

Thereafter, passaging points gradually decreased until they reached a plateau of approximately 7 days where it stabilized. In contrast, hESC colonies cultured on MATRIGEL had passaging points after an average of 10 days, and passage points were independent of the passage cycle. A detailed morphological analysis of hESCs cultured on PMEDSAH or MATRIGEL revealed several noteworthy aspects. For example, in contrast to MATRIGEL, where hESCs initially formed small colonies that increased in size and cell number over the next few days (Amit et al., 2003), several embryoid body-like structures and few small colonies were initially observed on the synthetic PMEDSAH hydrogel. Within a few days, growth on PMEDSAH hydrogels demonstrated EB-like structures attached to the hydrogel and hESC proliferation started forming colonies with defined borders and cells with high nucleus to cytoplasm ratio. Additionally, the shape of the initial colonies resembled cell colonies typically encountered for hESCs grown on MEF, and hESCs cultured on the synthetic hydrogel, but not on MATRIGEL, underwent an adaptive growth curve. While all pluripotency markers as well as karyotyping indicates that the undifferentiated cell state of hESCs cultured on PMEDSAH remained unchanged, the gradual decrease of passaging points with increasing passage cycles indicates the ability of hESCs to adapt to this specific synthetic cell matrix.

As described herein, hESCs cultured on PMEDSAH have been propagated for at least eighteen passages during 7 months. All PMEDSAH plates (more than 300 from 20 different batches) successfully support hESC attachment, growth and proliferation, thereby demonstrating that the synthetic substrates as described herein can be synthesized reproducibly with reliability. As well, PMEDSAH-coated plates were stored for several weeks to months and were UV sterilized prior to use, and neither storage nor sterilization negatively affected their ability to support hESC growth and proliferation. In addition, hESCs cultured on PMEDSAH have been cryopreserved using a controlled-rate freezer, thawed, and seeded again effectively on synthetic PMEDSAH matrices.

I. Polymers

As described above, in some embodiments, the present invention provides synthetic polymer substrates for the growth and maintenance of stem cells or embryos. The present invention is not limited to a particular polymer. In certain embodiments, the polymer has a zwitterionic group. In some exemplary embodiments, the zwitterionic group is

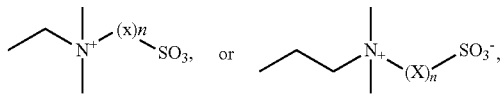

where x is any aliphatic or substituted aliphatic chain, any aryl or substituted aryl chain or hydrogen; and n is an integer of 1 or greater. In some embodiments, the zwitterionic group is MEDSAH or MAPDSAH. In other embodiments, the zwitterionic group is a zwitterionic group described, for example, in U.S. Pat. No. 6,395,800, herein incorporated by reference. In certain embodiments, the zwitterionic group contains phosphate and/or phosphonate groups as the anionic group. For example,

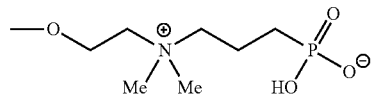

is a zwitterionic phosphonate group that may be employed. In another embodiment, the invention is also not limited to end-standing phosphate groups. In fact, 2-Methacryloyloxyethyl phosphorylcholine is another zwitterionic phosphate group that is suitable. In further embodiments, the zwitterionic group comprises a moiety with the following structure:

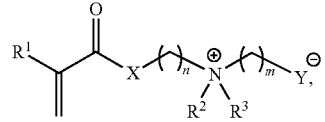

wherein R1, R2, and R3 are the same or different alkyl groups; wherein X is O, NH, or NR4 (e.g., wherein R4 is an alkyl group or any other type of organic moiety); and wherein Y is a sulfonate, a phosphonate, or a phosphate.

II. Uses of Synthetic Polymer Substrates

In one embodiment, the present invention provides for synthetic polymer substrates for use in tissue engineering. For example, compositions as described herein find use as a scaffold for growth of cells and tissues for implantation or transplantation into a subject, such as a human. As such, some embodiments of the present invention comprise methods for growing cells and tissues on scaffolds comprising synthetic polymer substrates as defined herein, wherein such scaffolds are used to grow cells in vitro or in vivo. For example, cells and tissues grown on in vitro scaffolds are used to grow cells and tissues for use in, for example research purposes and for implantation or transplantation into subjects as a treatment of a condition or disease. Scaffolds comprising the synthetic polymer matrices as described herein can also be implanted on, or into, a subject thereby aiding in seeding of cells for growth or regeneration of cells and tissues in a particular area or location of a subject to treat a disease or condition.

As such, the present invention provides compositions and methods for defined synthetic substrates for stem cell (e.g., adult or embryonic stem cell) culture, such as PMEDSAH, which represents a system for elimination of xenogeneic components in stem cell derivation and culture. In some embodiments, the present invention provides methods of using the synthetic matrices as described herein to grow and maintain cells (e.g., stem cells such as adult or embryonic stem cells) or embryos useful for fundamental research, cell based therapies, clinical disease applications, therapeutic discoveries, drug screening, toxicology testing, and regenerative medicine. In some embodiments, culture methods utilize fully defined media (e.g., available from Stem Cell Sciences, San Francisco, Calif.), other commercially available media, or other suitable culture media) in combination with the compositions of embodiments of the present invention.

In certain embodiments, the synthetic polymer matrixes of the present invention are employed for uses including, but not limited to, derivation of normal embryonic stem cells; differentiation of normal embryonic stem cells into different lineages; derivation of induced pluripotent stem (iPS) cells reprogrammed from somatic cells; culture of adult stem cells; stem cell culture in defined conditions for drug screening; derivation of genetically abnormal ES cells; differentiation of genetically abnormal embryonic stem cells into different lineages; derivation and differentiation of ES cells from individual or small clumps of undifferentiated blastomeres; derivation and differentiation of ES cells from individual or small clumps of early differentiated blastomeres; solid-state cell differentiation and organogenesis; growth and development of gametes in vitro; and embryo selection.

EXPERIMENTAL

The following examples are provided in order to demonstrate and further illustrate certain preferred embodiments and aspects of the present invention and are not to be construed as limiting the scope thereof.

Example 1

Human ESC Culture

Figure 3:
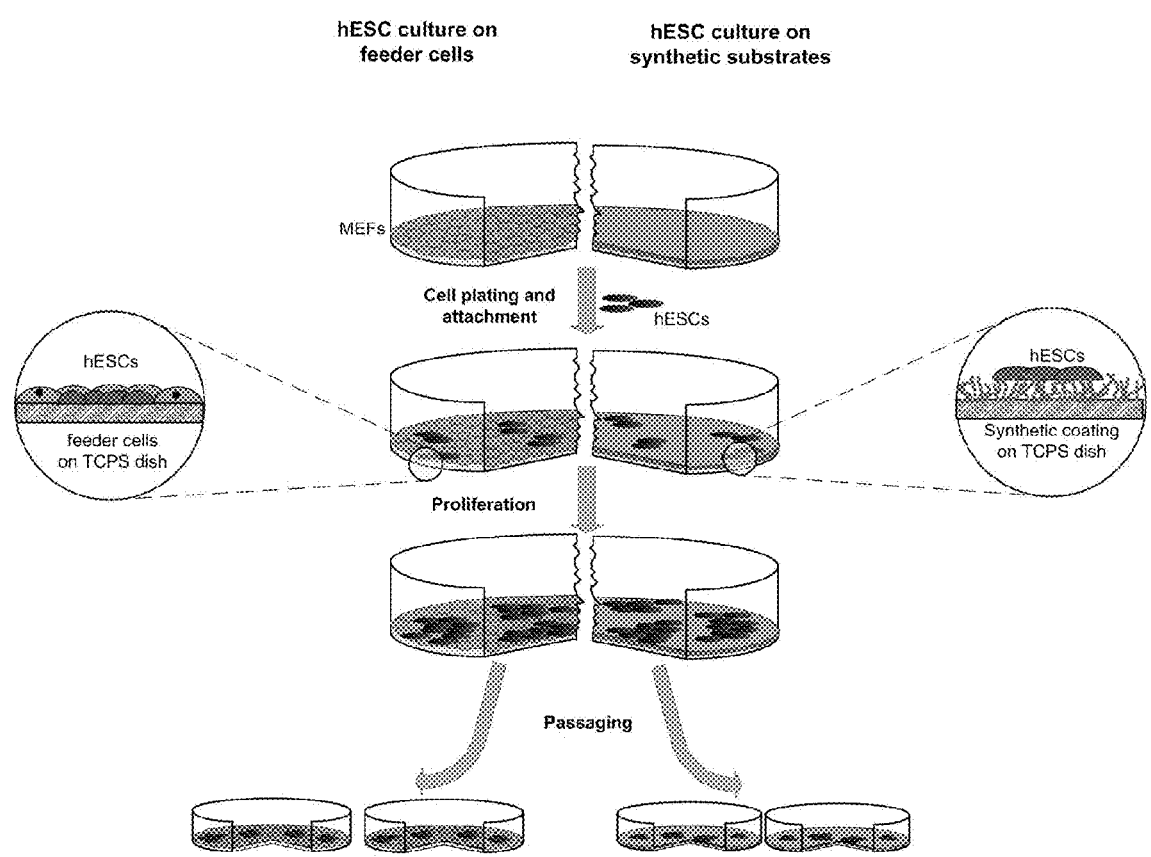
FIG. 3 shows a depiction of the seeding, proliferation and passaging of hESCs cells on MEFs or an exemplary synthetic substrate.

The culture medium for hESCs growing on irradiated mouse embryonic fibroblast (MEF) cells consisted of DMEM/F12 supplemented with 20% knockout serum replacement, 0.1 mM β-mercaptoethanol, 1 mM L-glutamine, 1% nonessential amino acids and 4 ng/ml human recombinant basic fibroblast growth factor. To obtain MEF-conditioned media (MEF-CM), irradiated MEFs ($8\times10^6$) were seeded on pre-gelled culture plate dishes. Twenty-four hours after plating, media was replaced for hESC culture media (60 ml), left in contact with MEFs to be conditioned for 24 h, and collected. Mouse embryonic fibroblasts were again fed with hESC culture media daily and used for 4 day CM collection. The CM was frozen at $-20°$ C. until use, and before use it was supplemented with additional 0.1 mM β-mercaptoethanol, 2 mM L-glutamine, and 4 ng/ml bFGF. Passage of undifferentiated colonies was done manually cutting small clumps of cells. Criteria for passage was when greater than 50% of colonies reached a mean diameter of 1 cm or greater and had an architecture of 2-3 cell layers thick (FIG. 3).

Substrates were prepared on tissue culture polystyrene plates (TCPS; 35 mm; Becton Dickinson and Co, Franklin Lakes, N.J.). Bare TCPS and MATRIGEL-coated plates were used as controls. MATRIGEL-coated plates were prepared with MATRIGEL (BD BioSciences, San Jose, Calif.) diluted 1:20 in cold DMEM/F12 at placed at $4°$ C. overnight, or at room temperature for 2 h. Coating of HEMA, MEDSAH, PEGMA and SMPS onto PTCP was done by activation of the polystyrene surface and initiation of graft-copolymerization of methacrylate monomers using UV-ozone. Both PLGA and PLA coatings were created by casting polymer films in a Teflon dish and attaching these films to PTCP afterwards.

For MEDSAH, the surface of the substrate was activated using the UV-Ozone generator for 40 min. Graft polymerization onto the polystyrene surface was carried out at $80°$ C. with a solution of 0.25M MEDSAH in a 4:1 Mixture of water and ethanol. The polymerization reaction was performed for 2 hours. The substrates were then washed in DI-water at $40$-$50°$ C. for 1 hour and dried under nitrogen.

Example 2

Synthetic Substrate Characterization

Coating presences were confirmed using Fourier transformation infrared spectroscopy (FTIR), X-ray photoelectron spectroscopy (XPS), and imaging ellipsometry. Surface morphology of coatings was elucidated using scanning electron microscopy (SEM) and atomic force microscopy (AFM). Synthetic substrates plates were maintained at room temperature in desiccators and were exposed to UV-light for 15 min before using. Prior to cell seeding, all surfaces were washed twice with PBS, MEF-CM was added, and the plates were incubated at $37°$ C. in 5% $CO_2$ overnight.

Example 3

Immunostaining

Immunostaining on cultured cells was performed to evaluate whether the synthetic substrates could maintain the hESCs in an undifferentiated state. For detecting OCT3/4, SOX-2, SSEA-4, TRA-1-60 and TRA-1-81, cells were fixed with 2% paraformaldehyde at room temperature for 15 min followed by permeabilization with 0.1% Triton X-100 for 10 min. All antibodies were detected with flourescein isothiocyanate (FITC)-labeled secondary antibody except for OCT3/4, which was detected with Texas Red-labeled secondary antibody. Cells were typically evaluation at the $5^{th}$, $10^{th}$ and $15^{th}$ passages. It was determined that the large majority of hESCs remained undifferentiated, with a low incidence (<5%) of spontaneous differentiation observed.

Example 4

In Vitro Evaluation of Pluripotency

Figure 2:
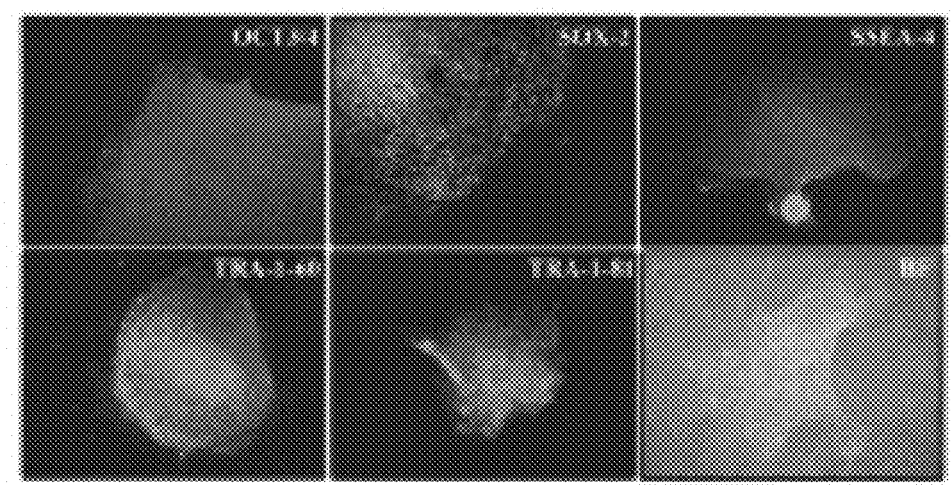
FIG. 2 demonstrates the detection of A) undifferentiated hESC markers as seen in hESCs grown on PMEDSAH coated substrates after multiple passaging. Markers detected include OCT3/4, SOX-2, SSEA-4, TRA-1-60 and TRA-1-81. The sixth frame demonstrates the staining hESC cells for pluripotency and normal colony morphology under phase contrast, and B) RT-PCR expression analysis of pluripotency markers; lane 1-no template control, lane 2-OCT ¾ and lane 3-SOX-2 from undifferentiated hESC colonies, lane 4-KRT-18 from ectoderm, lane 5-BMP-4 from mesoderm, lane 5-GATA-4 from endoderm found in embryoid bodies, and lane 7-actin control.
Figure 2:
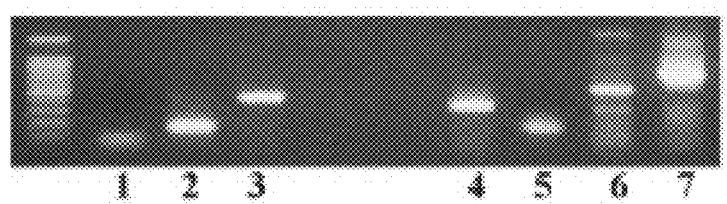

Embryoid bodies derived from clumps were cultured in suspension with culture medium without bFGF for four days and evaluated for pluripotency (FIG. 2, sixth frame).

Example 5

Reverse-Transcription PCR Analysis

RT-PCR was performed from total RNA extracted from cells and EBs with TRIzol reagent (Invitrogen) following manufacturers protocol, and SuperScript™ One-Step RT-PCR with Platinum® Taq (Invitrogen) was used for RT-PCR. One microgram of total RNA plus 20 pmol of forward and reverse primers were used in a 50 µl reaction. The cDNA synthesis and pre-denaturation were carried out in one cycle of $48°$ C. for 45 min, followed by one cycle at $94°$ C. for 2 min. PCR amplification was performed for 35 cycles at $94°$ C. for 15 sec, $54°$ C. for 30 sec, and $72°$ C. for 1 min. The final extension cycle was $72°$ C. for 8 min. Ten microliters of each PCR reaction were loaded onto a 1.0% agarose gel and size fractionated. Primers used were; undifferentiation cell markers: OCT ¾: (f) 5'-ctg cag tgt ggg ttt cgg gca-3' (SEQ ID NO: 1), (r) 5'-ctt gct gca gaa gtg ggt gga gga-3' (SEQ ID NO: 2); and SOX-2: (f) 5'-atg cac cgc tac gac g-3' (SEQ ID NO: 3), (r) 5'-ctt ttg cac ccc tcc cat tt-3' (SEQ ID NO: 4); for endodermal differentiation: GATA4: (f) 5'-ctc ctt cag gca gtg aga gc-3' (SEQ ID NO: 5), (r) 5'-gag atg cag tgt gct cgt gc-3' (SEQ ID NO: 6); for mesodermal differentiation: BMP4: (f) 5'-tga gcc ttt cca gca agt tt-3' (SEQ ID NO: 7), (r) 5'-ctt ccc cgt ctc agg tat ca-3' (SEQ ID NO: 8); for ectodermal differentiation: KRT18: (f) 5'-tct gtg gag aac gac atc ca-3' (SEQ ID NO: 9), (r) 5'-ctg tac gtc tca gct ctg tga-3' (SEQ ID NO: 10); and as a control, β-ACTIN: (f) 5'-atc tgg cac cac acc ttc tac aat gag ctg cg-3' (SEQ ID NO: 11), (r) 5'-cgt cat act cct gct tgc tga tcc aca tct gc-3' (SEQ ID NO: 12).

Example 6

Cytogenetic Analysis

Karyotype of hESCs growing on sulfonated hydrogels at passage 5 and 10 was performed. Chromosome preparation was done using standard protocols and the analysis by GTG banding method. At least 20 cells from each sample were examined by a qualified cytogeneticist.

Example 7

Cryopreservation and Thawing

Cryopreservation by controlled-rate freezing was performed followed a previously established protocol (Ware et al., 2005, Biotechniques 38:879-884), with some modifications. Briefly, clumps were suspended in 250 µl of freezing medium and placed in a 1.2 ml cryovial (Fisher Scientific, Pittsburgh, Pa.). The freezing medium consisted of DMEM (with 4.5 g/L of glucose; Invitrogen), 25% knockout SR (vol/vol), and 10% DMSO (Sigma, St. Louis, Mo.; vol/vol). Cryovials were placed inside a programmable freezing machine (CL-8000, Cryologic, Mulgrave, Victoria, Australia) and lowered from 20° C. to −10° C. at 2° C./min. At −10° C. cryovials were seeded and 5 minutes later the cooling cycle started decreasing 1° C./min to −33° C. Cryovials were then plunged into liquid nitrogen ($LN_2$), held for at least 5 min at −196° C. and maintained in the vapor phase of $LN_2$ ($VLN_2$). Clumps were thawed rapidly by removing the cryovials from $VLN_2$ storage and plunging them directly into 37° C. bath for 1 min. Thawed clumps were washed with culture medium and plated on sulfonated hydrogel plates.

Example 8

Synthetic Polymer Coatings for Long-Term Maintenance of Undifferentiated Human Embryonic Stem Cell Growth A. Methods Cell culture. Culture medium for hESCs growing on irradiated MEFs consisted of standard Dulbecco's modified Eagle's medium/F12 (DMEM/F12; GIBCO, Carlsbad, Calif.) supplemented with 20% KnockOut serum replacement (GIBCO), 0.1 mM β-mercaptoethanol, 1 mM L-glutamine, 1% non-essential amino acids and 4 ng/ml human recombinant basic fibroblast growth factor (bFGF) (Xu et al., Nat. Biotechnol. 19:971 [2001]). To obtain MEF-CM, irradiated MEFs ($8 \times 10^6$ cells) were seeded onto gelatin coated culture dishes in medium composed of high glucose DMEM, 10% fetal bovine serum (FBS), 1% non-essential amino acids, and 200 mM L-glutamine. After 24 h, MEF culture medium was replaced with the hESC culture medium described above (60 ml). This medium was left in contact with MEFs and was collected as MEF-CM after 24 h of conditioning. Media exchange was conducted daily and MEF-CM was collected for 3 days. The MEF-CM was frozen at −20° C. until use, when it was supplemented with 0.1 mM β-mercaptoethanol, 2 mM L-glutamine, and 4 ng/ml bFGF just prior to use (Xu et al., supra). Undifferentiated colonies were mechanically passaged by cutting small clumps of cells when more than 50% of the colonies attained a mean diameter greater than 1 cm and a thickness of 2-3 cell layers.

Cell-culture substrate synthesis. All polymer coatings were prepared on TCPS dishes (35 mm; Becton Dickinson and Co, Franklin Lakes, N.J.). Matrigel-coated and bare TCPS dishes were used as controls. Matrigel (BD BioSciences, San Jose, Calif.) was diluted 1:20 in cold DMEM/F12, applied to the dishes, and coating was allowed to form at 4° C. for overnight or at room temperature for 2 h. Graft-co-polymerization of methacrylate polymers onto TCPS surfaces was carried out using a 0.25 M solution of methacrylate monomers (Sigma-Aldrich, MO) in a 4:1 mixture of water and ethanol (Wu et al., Biomed Microdevices 8:99 [2006]). The TCPS dishes were activated using a UV-ozone generator (Jelight Co. Inc) for 40 min. Surface-activated dishes were immersed into the monomer solution which was heated to 80° C. for 2.5 h. The TCPS dishes were allowed to cool to 50° C. and were rinsed with a warm saline solution (0.9% NaCl, at 50° C.). Polymer coated dishes were left overnight in saline solution at 50° C. The dishes were cleaned by ultra-sonication in DI-water and dried under a stream of nitrogen gas. Both PLA (Sigma-Aldrich, MO) and PLGA (75:25; Sigma-Aldrich, MO) films were cast in a Teflon dish (diameter of 15 cm) by dissolving the polymer (1 g) in chloroform (50 ml) and allowing the solvent to evaporate. The film was carefully peeled off the Teflon dish after 2 days and cut into the requisite size. After extensive washing in DI-water and drying under vacuum, the casted film was attached to the TCPS dish.

Characterization of polymer coatings and preparation for cell culture. Presence of polymer coatings was confirmed using FTIR spectroscopy (Nicolet 6700 spectrometer) in the attenuated total reflectance (ATR) mode with a ZnSe 45° crystal. Elemental analysis was conducted using XPS (Axis Ultra XPS, Kratos Analyticals, UK) equipped with a monochromatized Al Kα X-ray source. The spectra were referenced to an unfunctionalized aliphatic carbon at 285.0 eV. Thickness of the coatings was recorded at a wavelength of 532 nm using $EP^3$-SW imaging ellipsometry (Nanofilm Technology GmbH, Germany). Four-zone nulling was performed at an angle of incidence of 58° and an anisotropic Cauchy parameterization model was used for curve fitting. Surface morphology of coatings was elucidated using SPM. Polymer-coated dishes were stored in desiccators at room temperature. Before cell seeding, dishes were sterilized by exposure to UV-light for 15 min and were washed twice with PBS. Finally dishes were incubated with MEF-CM overnight at 37° C. in a 5% $CO_2$ atmosphere.

Immunostaining. The cells were fixed in 2% paraformaldehyde for 30 min at room temperature and then permeabilized with 0.1% Triton X-100 for 10 min. Primary antibodies were diluted in 1% normal donkey serum and incubated overnight at 4° C. Fluorescein isothiocyanate (FITC)-labeled secondary antibodies were used to detect SOX-2 (Chemicon, Billerica, Mass.), TRA-1-60 (Chemicon), TRA-1-81 (Chemicon) and smooth muscle actin antibodies (DakoCytomation, Denmark). For the detection of OCT3/4 (Santa Cruz Biotechnology Inc., Santa Cruz, Calif.), SSEA-4 (Developmental Studies Hybridoma Bank, Iowa University), β III tubulin (Sigma) and α-fetoprotein (Sigma) antibodies, Texas red-labeled secondary antibodies were used. Samples were imaged using phase-contrast and fluorescent microscopy.

Image analysis. Cell nuclei count was performed with Image J 1.37v on photomicrographs of hESC colonies stained with Hoechst 33258 nuclear staining and either Oct3/4 or Sox-2 antibodies. Then, the percentage of cells positive to either antibody was calculated and compared among colonies culture on PMEDSAH- and Matrigel-coated plates. Unpaired t test was used to calculate the p value.

In vitro evaluation of pluripotency. Pluripotency was evaluated by embryoid body formation at 5, 10, 15 and 20 passages. Embryoid bodies derived from clumps of undifferentiated hESC colonies were cultured in suspension in a medium lacking bFGF to promote differentiation for 10 days. Alternatively, hESCs were allowed to overgrow in differentiation medium for 10 days.

Extraction and purification of total RNA from hESCs and EBs. After manually scrap, cells were pelleted by centrifugation at 800×g in RNase-free, 1.5 ml siliconized microcentrifuge tubes (Ambion, Austin, Tex.). Pellets were disrupted by vigorous pipeting in 800 µl of Trizol Reagent (Invitrogen, Carlsbad, Calif.). This solution was transferred to 2 ml PhaseLoc-Heavy tubes (Eppendorf, Hamburg, Germany), 200 µl of chloroform were added/800 µl of Trizol, and the tubes were centrifuged at maximum speed (13,000× g) in a microcentrifuge. The aqueous phase containing RNA was removed and additionally purified using the RNeasy Mini-Kit (Qiagen, Valencia, Calif.) following the manufacturer's RNA Clean-up protocol with the optional On-column DNase treatment; following the Qiagen protocols. RNA quality was checked using RNA 6000 Nano Assays performed on the Bioanalyzer 2100 Lab-on-a-Chip system (Agilent Technologies, Palo Alto, Calif.).

Reverse-transcription PCR analysis. Total RNA was reverse transcript using SuperScript™ One-Step RT-PCR with Platinum® Taq (Invitrogen) was used. In a single reaction (50 µl), 1 µg of total RNA and 20 pmol of forward (f) and reverse (r) primers were used (Table 4). The cDNA synthesis and pre-denaturation were carried out in the first cycle at 48° C. for 45 min, followed by a second cycle at 94° C. for 2 min. The PCR amplification was performed for 35 cycles at 94° C. for 15 sec, 5° C. for 30 sec, and 72° C. for 1 min. The final extension cycle was operated at 72° C. for 8 min. Finally, 10 µl of PCR reaction products were loaded onto a 1.0% agarose gel and size-fractionated.

Microarray analysis. Total RNA (10 µg) from cells was hybridized to Affymetrix Human Genome U133 Plus 2.0 microarray (Affymetrix; Santa Clara, Calif.) following the manufacturer's instructions. Data analysis was performed using a Robust Multi-array average that converted the plot of perfect match probe into an expression value for each gene (Irizarry et al., Biostatistics 4:249 [2003]). Based on a variance of 0.05, all the probe sets that did not appear to be differentially expressed in any samples were filtered and removed. The fit a linear model were using to increase the power of microarray analysis (Smyth et al., Bioinformatics 21:2067 [2005]).

Microarray validation by real time-PCR analysis. Total RNA was reverse-transcribed using MultiScribe™ Reverse Transcriptase System (Applied Biosystems; Foster city, CA). The ABI 7300 PCR and Detection System (Applied Biosystems) with SYBR® Green PCR Master Mix (Applied Biosystems) was used in real time-PCR. PCR was conducted in triplicate for each sample. Primers were indicated in Table 4. Human Actin was amplified as an internal standard. Reported values were calculated using ΔΔCt method, normalized against endogenous Actin.

Cytogenetic analysis. Karyotype analysis of hESCs was performed at 5, 10, 15 and 20 passages by cytogeneticists at Cell Line Genetics. Chromosomes were prepared using standard protocols and measurement was done using the GTL-banding method on at least 20 cells.

B. Results

Figure 4:
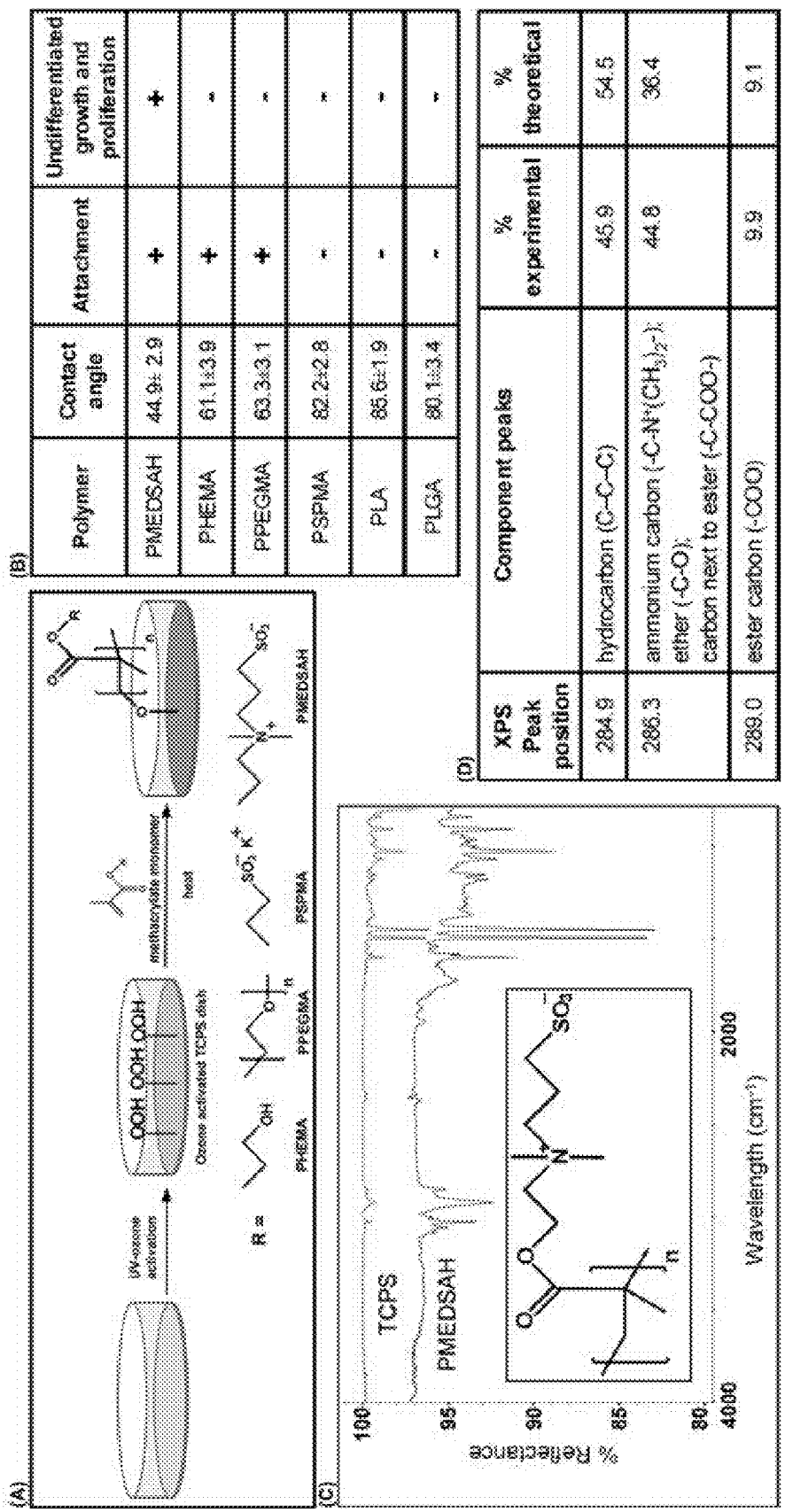
FIG. 4 shows synthesis and characterization of polymer coatings (A) Schematic description of surface-initiated graft-polymerization used to deposit different synthetic polymer coatings onto TCPS dishes. (B) Comparison of the synthetic polymer coatings based on contact angle, attachment of hESCs, and initial undifferentiated growth and proliferation. (C) FT-IR spectrum of PMEDSAH polymer coated and uncoated TCPS surfaces. (D) Characteristic signals from high resolution C1s XPS spectrum of PMEDSAH.

A chemically diverse group of synthetic polymer coatings was selected for cell adhesion studies. To ensure structural consistency between different materials, polymer materials were selected that shared an identical polymer backbone structure, but differed in their side chain chemistries. In addition, the same fabrication method, surface-initiated graft-polymerization, was used to deposit all synthetic polymer coatings onto tissue culture polystyrene (TCPS) dishes (FIG. 4A). As shown in FIG. 4B, differences in side chains result in synthetic polymer coatings with high to moderate hydrophilicity (based on contact angle measurements). Based on side chain chemistries, polymer coatings can be classified as hydrogen-bond acceptors (poly[2-hydroxyethyl methacrylate], PHEMA), hydrogen-bond donors (poly[poly (ethylene glycol)methyl ether methacrylate], PPEGMA), charge-donors (poly[3-sulfopropyl methacrylate], PSPMA), or polyzwitterions (PMEDSAH). This group of polymer coatings was compared to two solvent-cast poly(α-hydroxy esters), PLA and PLGA, as well as Matrigel-coated and unmodified TCPS dishes. Two federal approved hESC lines (H9, NIH code: WA09; WiCell, Madison, Wis.; and BG01, NIH code: BG01; BresaGen, Inc., Athens, Ga.) were used throughout the study. Colonies of hESCs previously cultured on mouse embryonic fibroblasts (MEF) were mechanically harvested and transferred onto polymer-coated cell culture dishes using the approach illustrated in FIG. 3. All cell culture experiments were conducted with MEF-conditioned medium (MEF-CM), which supports hESC growth and proliferation (Xu et al., supra). This approach enables delineation of influences of the matrix versus medium.

During initial cell passages on PLA and PLGA coatings, no hESC attachment was observed. PHEMA, PPEGMA and the negatively-charged PSPMA coatings as well as unmodified TCPS dishes supported initial hESC attachment and proliferation, but the majority of colonies spontaneously differentiated during the first (PPEGMA-coated dishes) or second passage (PHEMA, PSPMA and unmodified TCPS dishes), and propagation of undifferentiated cells was not possible (FIG. 4B). These findings are consistent with a recent study that reported short-term hESC attachment and proliferation on peptide-modified PNIPAAm matrices (Li et al., Journal of Biomedical Materials Research, Part A 79A, 1-5 [2006]). However, a completely different result was observed on PMEDSAH coatings: hESCs not only adhered and proliferated on these surfaces, but also expressed characteristic pluripotent stem cell markers and transcription factors such as OCT3/4, SOX-2, SSEA-4, TRA-1-60 and TRA-1-81, which are associated with the undifferentiated state of hESCs. Based on these short-term adhesion studies, the surfaces were categorized into three groups: (1) Polymer coatings that did not support hESC adhesion (PLA, PLGA, and PSPMA); (2) polymer coatings that supported initial adhesion, but resulted in subsequent differentiation (PEGMA, PHEMA, and TCPS); and (3) polymers that supported adhesion and undifferentiated growth of hESCs (PMEDSAH, Matrigel).

To further characterize the supportive role of PMEDSAH coatings for long-term hESC growth and passaging, a more detailed assessment of the physico-chemical and structural properties of PMEDSAH hydrogel coating was undertaken. One of the most prominent characteristics of PMEDSAH is the presence of zwitterionic sulfobetaine groups. As shown in FIG. 3A, negatively-charged sulfonate and positively-charged quaternary ammonium groups coexist in PMEDSAH in the form of sulfobetaines. This molecular structure results in unusually high localized dipole moments of 23

D23 oriented parallel to the surface while maintaining a net neutral surface. As a result, PMEDSAH can engage in strong inter- and intramolecular dipole interactions, and exist as non-associated as well as fully associated structures (Azzaroni et al., Angewandte Chemie, International Edition 45, 1770-1774 [2006]). Such complex structural behavior is not present in the other synthetic polymer coatings included in this study, but is frequently encountered in naturally-derived materials, such as proteins, which are often considered as prime examples of zwitterionic molecules (Harris et al., Biochemical J. 24:1080 [1930]). Surfaces that present zwitterionic sulfobetaine groups have been used as biomedical coatings or protein-resistant surfaces (Yuan et al., Colloids Surf B Biointerfaces 35, 1-5 [2004]; Jiang et al., Colloids Surf B Biointerfaces 36, 19-26 [2004]; Cho et al., Langmuir 23, 5678-5682 [2007]).

To fabricate synthetic cell culture matrices, PMEDSAH coatings were polymerized on the surfaces of TCPS dishes using a grafting-from approach. Compared to alternate surface modification techniques, such as tethering of polymer chains onto the surface, this approach is known to result in higher surface densities (Zhao et al. Progress in Polymer Sci 25:677 [2000]). After grafting, PMEDSAH coatings were characterized using a combination of surface analytical tools which included X-ray photoelectron microscopy (XPS), Fourier transform infrared spectroscopy (FT-IR), imaging ellipsometry, and scanning probe microscopy (SPM). The polymer coatings had an average thickness of 200 nm, as determined by imaging ellipsometry and an average root mean square (RMS) surface roughness of 0.91 nm, which was determined by SPM. Contact angle measurements revealed an advancing contact angle of 45°, which is in accordance with a self-associated super-coiled regime (Arasawa et al., Reactive and Function Polymers 61: 153 [2004]). On the basis of these data, the resulting polymer coatings are best described as ultra-thin, smooth polymer films consisting of coiled sub-domains chemically tethered to the TCPS surface. Further information regarding the chemical identity of these coatings was revealed by the FT-IR spectrum of the polymer coating (FIG. 4C). Distinct bands were identified at 1724 $cm^{-1}$ and 1196 $cm^{-1}$ indicated the presence of carbonyl groups and sulfonate groups respectively and clearly identified the PMEDSAH polymer coatings. To further confirm initial evidence from FT-IR studies, the elemental composition of PMEDSAH was quantified by means of XPS. Presence of characteristic signals associated with nitrogen were found at 402.0 eV, sulfur at 168.0 eV, and oxygen at 532.0 eV. The relative composition of these elements showed good agreement with the expected chemical composition of PMEDSAH. In addition, the high resolution C1s XPS spectrum of PMEDSAH revealed characteristic signals associated with hydrocarbon (C—H/C) at 285.0 eV, ammonium-bond carbon (—C—N+(CH3)2-) at 286.4 eV, and ester carbon (—COO—) at 288.9 eV (FIG. 4D). Taken together, FT-IR and XPS analyses not only established the chemical composition of PMEDSAH coating, but also provided strong evidence for the presence of zwitterionic groups at the coating surface (Lahann et al., Macromolecules 35:4380 [2002]). Owing to their supportive influence on hESC adhesion and proliferation in short-term experiments together with their unusual chemical properties, PMEDSAH coatings clearly distinguished themselves from other synthetic polymers studied here and elsewhere (Anderson et al., Nature Biotechnology 22:863 [2004]; Ilic, Regenerative Medicine 1:95 [2006]).

Figure 5:
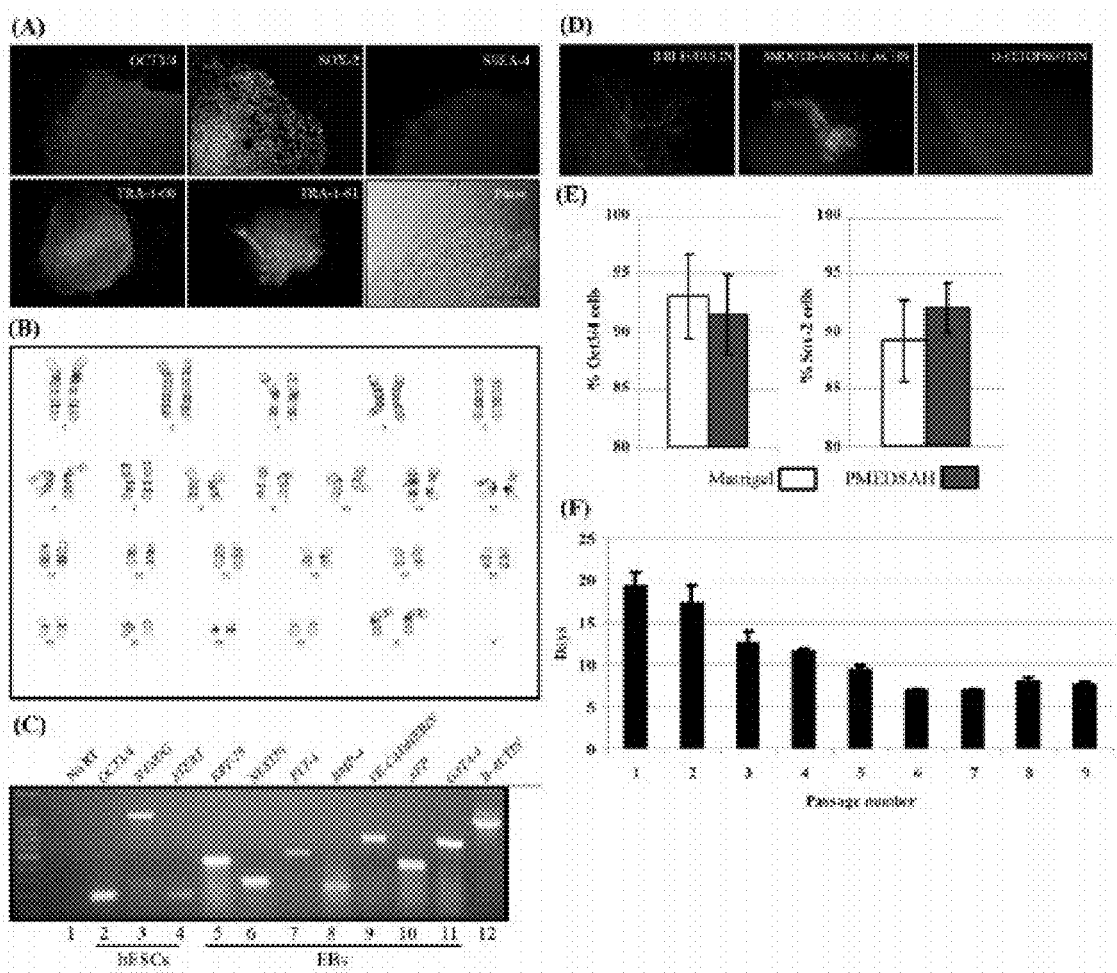
FIG. 5 shows Characterization of hESCs cultured on PMEDSAH. (A) Human ESCs on PMEDSAH expressed ESC markers such as OCT3/4, SOX-2, SSEA-4, TRA-I-60 and TRA-1-81. (B) Standard GTL-banding analysis revealed that hESCs maintained a normal female karyotype throughout the study. (C) RT-PCR analysis of expression of markers of pluripotency (lane 2: OCT3/4; lane 3: NANOG; lane 4: hTERT) from undifferentiated hESC colonies and from ectoderm (lane 5: KRT-18; lane 6: NESTIN), mesoderm (lane 7: FLT-1; lane 8: BMP-4; lane 9: VE-CADHERIN) and endoderm (lane 10: AFP; lane 11: GATA-4) found in EBs. Negative control (Lane 1: no template) and positive control (lane 12: ACTIN). (D) When differentiation was induced in hESCs maintained on PMEDSAH, positive immunoreactivity was identified for β III tubulin, smooth muscle actin and α-fetoprotein, indicating the presence of ectoderm, mesoderm and endoderm respectively. Scale bar is 200 μm. (E) Percentage (average±SEM) of Oct3/4 and Sox-2 positive cells on hESC colonies culture on PMEDSAH- and Matrigel-coated plates at passage 20. (F) Human ESCs growing on PMEDSAH showed an adaptive growth curve and reached a passage-time plateau of 8±1 days (average±SEM).

To evaluate long-term impact of PMEDSAH hydrogel surfaces on stem cell culture, hESCs were mechanically passaged to PMEDSAH- and Matrigel-coated dishes. The cells were monitored at regular intervals using karyotyping, expression of ESC markers and in vitro evaluation of pluripotency. It was found that dishes coated with PMEDSAH supported cell attachment, colony growth, and hESC proliferation for over 8 months. After 5, 10, 15 and 20 passages on PMEDSAH, hESCs were examined by immunostaining, and they expressed pluripotency markers including OCT3/4, SOX-2, SSEA-4, TRA-1-60 and TRA-1-81 (FIG. 5A). Standard GTG-banding analysis, after every fifth passage, revealed that hESCs maintained a normal karyotype (FIG. 5B). Presence of a normal euploid karyotype demonstrates pluripotency. Long-term cultures of mouse31 and human32-35 ESCs have shown to bias for the occurrence of aneuploidy. PMEDSAH coatings have supported hESC culture for 20 passages over a period of 8 months retaining normal karyotype and pluripotency.

The pluripotency of hESCs was further validated in vitro by formation of embryoid bodies and detection of characteristic genes representative of the three embryonic germ layers: ectoderm (KRT-18 and NESTIN), mesoderm (FLT-1, BMP-4 and VE-CADHERIN) and endoderm (AFP and GATA-4) (FIG. 5C). Furthermore, hESCs were allowed to overgrow in a non-supportive medium followed by immunostaining with antibodies specific for β III tubulin (ectoderm), smooth-muscle actin (mesoderm) and α-fetoprotein (endoderm) to identify differentiated cells from the three germ layers (FIG. 5D).

Figure 6:
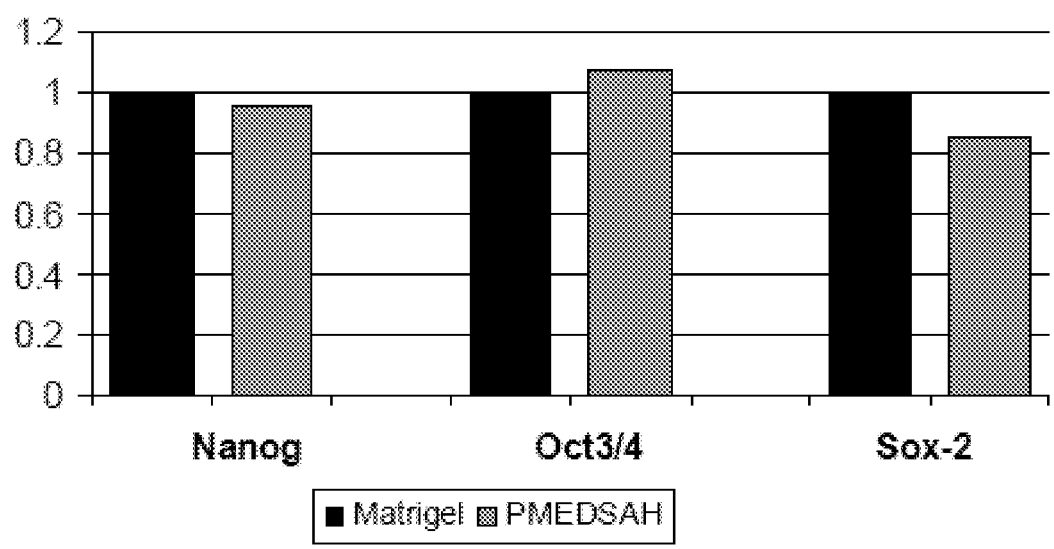
FIG. 6 results from Example 8 showing that genes of pluripotency such as nanog, Oct3/4 and Sox-2 were not significantly different expressed among hESCs cultured on PMEDSAH- and Matrigel-coated dishes.
Figure 7:
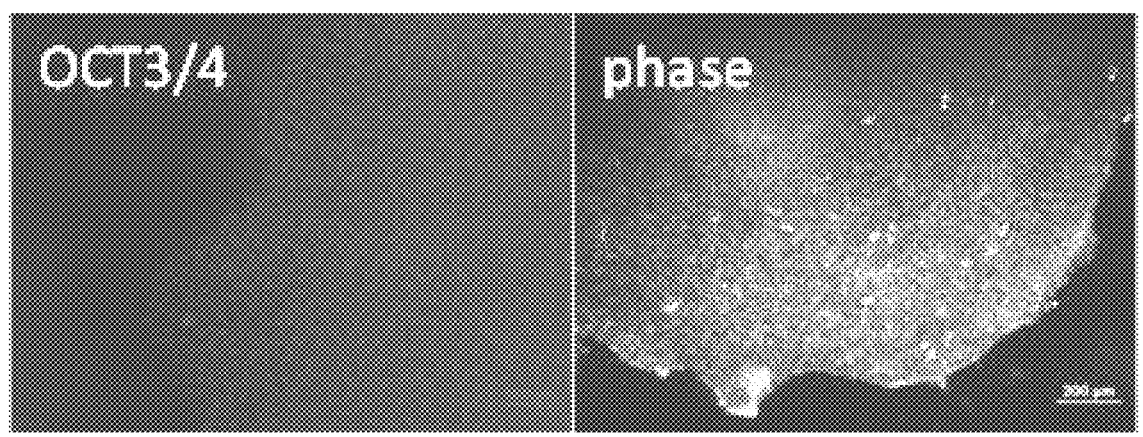
FIG. 7 shows fluorescence micrographs of colonies of hES cells cultured on PMAPDSAH in mTeSR1 medium showing expression of pluripotency marker OCT3/4 and phase-contrast image.
Figure 8:
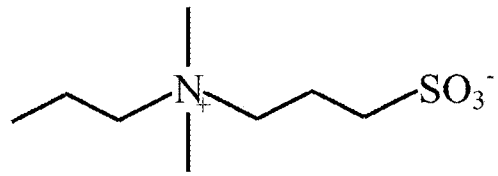
FIG. 8 shows the chemical structures of: Propyl dimethyl (3-sulfopropyl)ammonium hydroxide; generalized Propyl dimethyl(3-sulfoakyl)ammonium hydroxide; 3-(methacryloylamino)propyl dimethyl(3-sulfopropyl)ammonium hydroxide; and generalized 3-(methacryloylamino)propyl dimethyl(3-sulfoalkyl)ammonium hydroxide.
Figure 8:
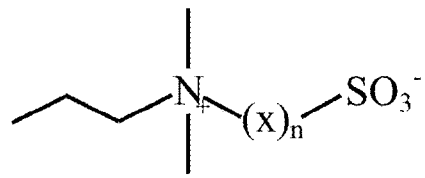
Figure 8:
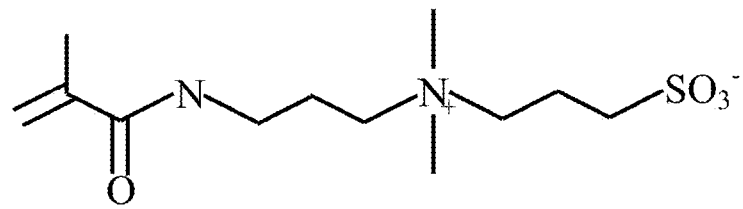
Figure 8:
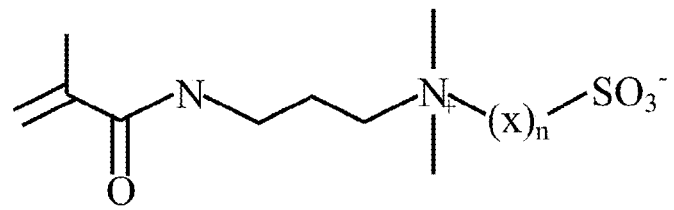
Figure 9:
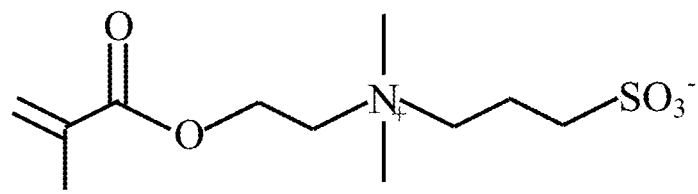
FIG. 9 shows the chemical structures of: 2-(methacryloyloxy)ethyl dimethyl(3-sulfopropyl)ammonium hydroxide; generalized 2-(methacryloyloxy)ethyl dimethyl(3-sulfoalkyl)ammonium hydroxide; and 2-(methacryloyloxy) ethyl dimethyl(3-phosphonylpropyl)ammonium.
Figure 9:
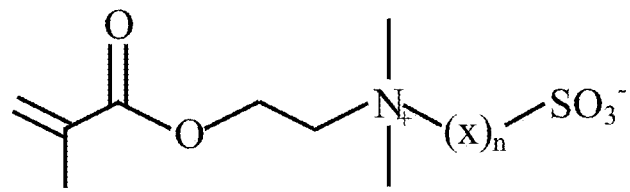
Figure 9:
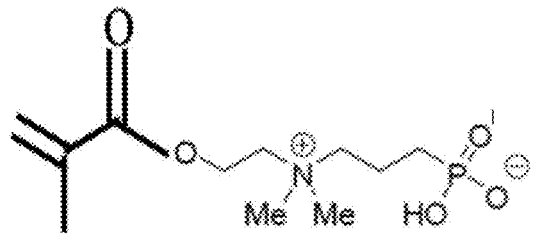

Throughout this study, phenotypic and genotypic characteristics of hESCs cultured on PMEDSAH coatings were indistinguishable from those on Matrigel-coated dishes. For example, at passage 20 the percentage of cells expressing Oct3/4 and Sox-2 for colonies grown on PMEDSAH-coated dishes was 91.40%±3.43 and 92.06%±2.22 respectively as against 93.00%±3.62 and 89.21%±3.52 for Matrigel-coated dishes (FIG. 5E). Validation by real time PCR analysis verified that genes of pluripotency such as nanog, Oct3/4 and Sox-2 were not significantly different expressed among hESCs cultured on PMEDSAH- and Matrigel-coated dishes (FIG. 6). In addition, microarray analysis was conducted to elucidate mechanistic differences between hESCs grown on PMEDSAH versus Matrigel. Only 23 genes (out of a total of 38,500 genes) were expressed at significantly different ($p \leq 0.05$) levels between cells culture on PMEDSAH- and Matrigel-coated dishes. The up and down regulated genes were members of calcium signaling and focal adhesion pathways (Table 2 for genes with identified pathway; Table 3 for complete list of different regulated genes).

While biochemical, histological and genetic analysis showed that hESCs cultured on PMEDSAH and Matrigel are identical, differences with respect to initial proliferation times were observed between hESCs cultured on PMEDSAH and Matrigel coatings. Time between passages, i.e., the time it takes for a cell population to attain cell densities sufficient for passaging, was monitored during long-term cell culture experiments. On Matrigel-coated dishes, hESCs initially formed small colonies that increased in size and cell number over the next few days. Time between passages was 10±2 days, independent of the passage number. On the other hand, hESC colonies cultured on PMEDSAH coatings required culture for 19±3 days prior to the first passage. Thereafter, the time between passages gradually decreased until a plateau of 8±1 days was reached after passage number 7 (FIG. 5E). While the expression of pluripotency markers and the ability to form new colonies indicated that hESCs cultured on PMEDSAH coatings remained undifferentiated, the observed proliferation kinetics show that hESCs cultured on PMEDSAH coatings experienced adaptive growth profiles.

During the course of this study, 300 PMEDSAH hydrogel dishes originating from more than 20 different fabrication batches successfully supported attachment, growth and proliferation of undifferentiated hESCs during 20 continuous passages, an indication that these synthetic substrates can be synthesized in a reproducible and reliable manner. Moreover, long-term storage and UV-sterilization of polymer coated dishes did not affect their ability to support hESC growth and proliferation. In addition, hESCs cultured on PMEDSAH hydrogels were cryopreserved, thawed and successfully re-seeded onto fresh PMEDSAH-coated dishes. Under long-term culture conditions, cells supported by PMEDSAH coatings were phenotypically stable, expressed appropriate pluripotency markers, maintained a normal karyotype, and retained the capacity to differentiate.

Development of PMEDSAH hydrogel coatings as the first fully-defined synthetic substrate for long-term hESC culture represents important progress toward the elimination of xenogenic, undefined, and labile components from the insoluble microenvironment used for hESC derivation and culture. This rationally designed culture matrix establishes a radical, rather than incremental diversion from previously exploited hESC support matrices and provides one of the missing links in future development of fully defined hESC microenvironments. A major advantage of fully synthetic matrices over naturally derived substrates is that there physico-chemical makeup can be altered in highly controlled ways opening the possibilities for more detailed mechanistic studies that not only aim at understanding the mechanisms behind the novel capabilities of PMEDSAH, but ultimately lead to entirely defined microenvironments consisting of synthetic matrices and synthetic media.

TABLE 2

| Pathway | Description | GenBank | Fold change |
|---|---|---|---|
| Jak-STAT signaling pathway | Suppressor of cytokine signaling 3 | AI244908 | −1.88 |
| Neuroactive ligand-receptor interaction | Neuropeptide FF receptor 2 | AF257210 | −1.75 |
| Calcium signaling pathway | Guanine nucleotide binding protein (G protein), alpha 14 | NM_004297 | −1.55 |
| Biosynthesis of steroids and terpenoid | Farnesyl-diphosphate farnesyltransferase 1 | BF438300 | −1.52 |
| Focal adhesion | Caveolin 1, caveolae protein, 22 kDa | NM_001753 | −1.48 |
| Purine, pyrimidine, nicotinate and nicotinamide metabolism | 5′-nucleotidase cytosolic II | AV700081 | −1.43 |
| Jak-STAT signaling pathway, cytokine-cytokine receptor interaction | Interleukin 13 receptor, alpha 1 | US1380 | −1.42 |
| Notch signaling pathway | Mastermind-like 2 (*Drosophila*) | BF358386 | −1.31 |
| Calcium signaling pathway, gap junction | GNAS complex locus | AF107846 | 1.52 |

TABLE 3

| Pathway | Description | GenBank | Fold change |
|---|---|---|---|
|  | Annexin A3 | M63310 | −2.01 |
| Jak-STAT signaling pathway | Suppressor of cytokine signaling 3 | AI244908 | −1.88 |
| Neuroactive ligand-receptor interaction | Neuropeptide FF receptor 2 | AF257210 | −1.75 |
|  | Glycoprotein M6A | D49958 | −1.66 |
|  |  | BC039495 | −1.62 |
| Calcium signaling pathway | Guanine nucleotide binding protein (G protein), alpha 14 | NM_004297 | −1.55 |
| Biosynthesis of steroids and terpenoid | Farnesyl-diphosphate farnesyltransferase 1 | BF438300 | −1.52 |
| Focal adhesion | Caveolin 1, caveolae protein, 22 kDa | NM_001753 | −1.48 |
|  | Caldesmon 1 | NM_018495 | −1.47 |
| Purine, pyrimidine, nicotinate and nicotinamide metabolism | 5′-nucleotidase cytosolic II | AV700081 | −1.43 |
|  |  | AL157496 | −1.43 |
|  | Glypican 6 | AK021505 | −1.42 |
|  | Nuclear factor I/B | AI186739 | −1.42 |
| Jak-STAT signaling pathway, cytokine-cytokine receptor interaction | Interleukin 13 receptor, alpha 1 | US1380 | −1.42 |
|  | Supervillin | NM_003174 | −1.40 |
|  | Chromosome 6 open reading frame 155 | BF500942 | −1.39 |
|  |  | AF194537 | −1.36 |
| Notch signaling pathway | Mastermind-like 2 (*Drosophila*) | BF358386 | −1.31 |
|  | Zinc finger protein 342 | AA761573 | 1.30 |
|  | Transcription elongation factor A (SII)-like 2 | AF063606 | 1.36 |
|  | Cripto, FRL-1, cryptic family 1 | AF312769 | 1.40 |
| Calcium signaling pathway, gap junction | GNAS complex locus | AF107846 | 1.52 |
|  | Zinc finger and BTB domain containing 24 | BC036731 | 1.55 |

TABLE 4

| Gene | Forward primer | Seq. ID | Reverse primer | Product (bp) | Seq ID |
|---|---|---|---|---|---|
| Reverse Transcriptase | | | | | |
| OCT3/4 | ctgcagtgtgggtttcgggca | 1 | cttgctgcagaagtgggtggagga | 168 | 2 |
| NANOG | cggcttcctcctcttcctctatac | 13 | atcgatttcactcatcttcacacgtc | 953 | 14 |
| hTERT | cggaagagtgtctggagcaa | 15 | ggatgaagcggagtctgga | 144 | 16 |
| KRT18 | tctgtggagaacgacatcca | 9 | ctgtacgtctcagctctgtga | 378 | 10 |
| NESTIN | cagctggcgcacctcaagatg | 17 | agggaagttgggctcaggactgg | 209 | 18 |
| BMP4 | tgagcctttccagcaagttt | 7 | cttccccgtctcaggtatca | 182 | 8 |
| VE-CADHERIN | acgggatgaccaagtacagc | 19 | acacactttgggctggtagg | 593 | 20 |
| FLT-1 | atcagagatcaggaagcacc | 21 | ggaacttcatctgggtccat | 451 | 22 |
| AFP | ccatgtacatgagcactgttg | 23 | ctccaataactcctggtatcc | 357 | 24 |
| GATA-4 | ctccttcaggcagtgagagc | 5 | gagatgcagtgtgctcgtgc | 574 | 6 |
| ACTIN | atctggcaccacaccttctacaatgagctgcg | 11 | cgtcatactcctgcttgctgatccacatctgc | 835 | 12 |
| Real-time PCR | | | | | |
| SOX2 | gagagaaagaaagggagagaag | 25 | gagagaggcaaactggaatc | 140 | 26 |
| NANOG | tcctcctcttcctctatactaac | 27 | cccacaaatcaggcatag | 112 | 28 |
| OCT3/4 | agtcagtgaacagggaatgg | 29 | tcgggattcaagaacctcg | 131 | 30 |
| Actin | gccgaggactttgattgc | 31 | gtgtggacttgggagagg | 143 | 32 |

TABLE 5

| Substrate | Contact angle (in dry state) | Percentage (±SEM) of attachment and colony formation | Percentage (±SEM) of cells positive to Oct3/4 | Percentage (±SEM) of cells positive to Sox-2 | Number of passages |
|---|---|---|---|---|---|
| Matrigel | Nm | 98 ± 2 | 93 ± 3.6 | 89.2 ± 3.5 | 20 |
| PMEDSAH | 17.1 ± 1.2 | 15 ± 1 | 91.4 ± 3.4 | 92.06 ± 2.2 | 20-still in progress |
| PHEMA | 56.0 ± 1.4 | 12 ± 1 | 0 | 0 | 2 |
| PPEGMA | 63.3 ± 3.1 | 5 ± 1 | 0 | 0 | 1 |
| PSPMA | 50.2 ± 4.1 | 14 ± 2 | | 91 ± 5 | 2-still in progress |
| PLA | 85.6 ± 1.9 | 0 | — | — | 0 |
| PLGA | 80.1 ± 3.4 | 0 | — | — | 0 |
| PMAPDSAH | 69.2 ± 4.7 | 7 ± 2 | — | — | Still in progress |
| PCBMA | 71.6 ± 4.9 | 0 | | | |
| PMETAC | 40.5 ± 5.8 | 8 ± 1 | 90 ± 2.3 | 90 ± 5.2 | 2-still in progress |
| TCPS | Nm | 8 ± 2 | 0 | 0 | 0 |

Example 9

Use of PMAPDSAH for Cell Culture

Poly[[3-(methacryloylamino)propyl]dimethyl(3-sulfopropyl)ammonium hydroxide] (PMAPDSAH) was coated on tissue culture polystyrene (TCPS) dishes using graft polymerization. The dishes were first activated using UV-ozone and immersed in a 0.25 M solution of the monomer in a 4:1 solvent mixture of water:ethanol. The reaction was carried out at 80 C for 4 h. The dishes were washed overnight in a 1% NaCl solution and rinsed with DI-water. Before hES cell culture, the polymer-coated dishes were sterilized using UV radiation overnight, washed with Dulbecco's Phosphate Buffered Saline (D-PBS) three times and pre-incubated with the mTeSR1 medium for 48 h. Aggregates of hES cells growing on MEFs were mechanically transferred to PMAPDSAH-coated dishes and allowed to attach for 48 h. The cell culture medium was changed after every 48 h and cells were passaged after 10 days. Fluorescence micrographs of colonies of hES cells cultured on PMAPDSAH in mTeSR1 medium showed expression of pluripotency markers: OCT3/4, SOX2, SSEA-4, TRA-I-60 and TRA-I-81. hES cells showed a normal karyotype.

Example 10

Use of Different Thicknesses of PMAPDSAH

Poly[[3-(methacryloylamino)propyl]dimethyl(3-sulfopropyl)ammonium hydroxide] (PMAPDSAH) with different thicknesses were fabricated using atom transfer radical polymerization (ATRP) by varying the concentration of copper(I) catalyst in the reaction mixture and the reaction time. Aggregates of hES cells growing on mouse embryonic fibroblasts (MEFs) were mechanically transferred to polymer-coated dishes and allowed to attach for 48 h. The cell culture medium was changed after every 48 h and cells were passaged after 10 days. Fluorescence micrographs of colonies of hES cells cultured on polymer-coated substrates in StemPro medium showed expression of pluripotency markers: OCT3/4, SOX2, SSEA-4, TRA-I-60 and TRA-I-81. hES cells showed a normal karyotype.

Example 11

Co-Polymers of PMEDSAH and PPEGMA

Co-polymers of Poly[2-(methacryloyloxy)ethyl dimethyl-(3-sulfopropyl)ammonium hydroxide] and poly(ethylene glycol methacrylate) were coated on tissue culture polystyrene (TCPS) dishes using graft polymerization. The dishes were first activated using UV-ozone and immersed in a 0.15 M solution of the monomers in a 4:1 solvent mixture of water:ethanol at 80 C for 2.5 h. The dishes were washed overnight in a 1% NaCl solution and rinsed with DI-water. The polymer-coated dishes were sterilized using ethanol followed by D-PBS. Human mesenchymal stem cells were trypsinized and added to the dishes at a density of 5000 cells/cm2. The cells were fed after every 48 h. The cells were tested for differentiation into adipogenic, chondrogenic, and osteogenic lineages.

Example 12

Use of PMEDSAH with Induced Pluripotent Cells

PMEDSAH was coated on TCPS dishes using graft polymerization. The dishes were first activated using UV-ozone and immersed in a 0.25 M solution of the monomer in a 4:1 solvent mixture of water:ethanol. The reaction was carried out at 80 C for 2.5 h. Human mesenchymal stem cells, primary human fibroblasts, or neuronal stem cells were cultured on PMEDSAH in the presence of xeno-free human cell conditioned medium. The cells were reprogrammed using retroviral supernatants expressing reprogramming factors OCT4, SOX2, KLF4, and c-MYC. Subsequently colonies of tightly-packed cells with a high nucleus-to-cytoplasm ratio and hES cell-like morphology appeared in the cultures. Fluorescence micrographs of colonies of induced pluripotent (iPS) cells cultured on polymer-coated substrates showed expression of pluripotency markers: OCT3/4, SOX2, SSEA-4, TRA-I-60 and TRA-I-81.

Example 13

Co-Polymers of PMEDSAH and PMETAC

Copolymer of PMEDSAH and poly(2-(methacryloyloxy)ethyl)trimethylammonium chloride (PMETAC) was fabricated using graft-copolymerization. The TCPS dishes were activated using UV-ozone and immersed in the monomer solution at 80 C for 3 h. Human neural stem (hNS) cells were transferred from laminin-coated dishes on to copolymer-coated dishes in the presence of serum-free STEMPRO NSC SFM media. Immunocytochemistry showed that hNS cells cultured in STEMPRO NSC SFM were positive for the neural stem cell-type specific markers nestin and SOX2, and the proliferation marker Ki67.

Example 14

Co-Polymers of HEMA and PMEDSAH

Copolymer of 2-hydroxyethyl methacrylate (HEMA) and PMEDSAH was synthesized using graft-copolymerization. The TCPS dishes were activated using UV-ozone and immersed in the monomer solution at 80 C for 3 h. Human umbilical vein endothelial cells (HUVECs) were trypsinized and added to the copolymer-coated dishes at a density of 1×105 cells/ml in the presence of endothelial growth medium (EGM). The cells were subsequently fixed and stained rhodamine-conjugated phalloidin (for actin filaments) and counterstained with Hoechst 33342 (for the nucleus).

Example 15

Effects of Gel Architecture on the Ability of Synthetic Polymer Coatings to Support Human Embryonic Stem Cell Self-Renewal In this Example, PMEDSAH films with different film thicknesses were prepared on tissue culture polystyrene using a combination of chemical vapor deposition (CVD) polymerization and atom transfer radical polymerization (ATRP) (Wang et al., 1995, herein incorporated by reference). Using films with different thicknesses, the extent to which gel architecture may influence critical hESC properties was determined.

Materials and Methods

Synthetic Surface Preparation and Characterization

CVD and Ellipsometry

The initiator used for ATRP was synthesized via chemical vapor deposition (CVD) polymerization of [2.2]paracyclophane-4-methyl 2-bromoisobutyrate. For CVD polymerization, around 30-40 mg of the precursor was loaded into the sublimation zone. Sublimation of the precursor occurred at 120° C., followed by pyrolysis at 540-550° C. After transfer of the reactive monomer species into the deposition zone, a thin film of poly[(p-xylylene-4-methyl-2-bromoisobutyrate)-co-(p-xylylene)] was coated onto the target substrates. Here, tissue culture polystyrene (TCPS) plates as well as surrogates (gold and silicon wafers) for chemical and physical analysis were placed onto a rotating stage of the deposition chamber and were maintained at 15° C. during CVD polymerization. Ellipsometry was performed on the silicon wafers to measure thickness of the initiator coating before and after ATRP. Film thickness was assessed with a multi-wavelength imaging null-ellipsometer (EP3 Nanofilm, Germany). Fixed values of the real (n=1.58) and imaginary (k=0) refractive index of the polymer coatings and the ellipsometric delta and psi were used to determine film thickness. It should be noted that the refractive index of the initiator coating was very close to that of PMEDSAH. After the reaction, thickness of the PMEDSAH coating was calculated by subtracting the initial thickness from the post-reaction thickness.

UVO-Initiated Grafting

The process was carried out in a fume hood with connections for argon and vacuum. A 500 mL reaction vessel was degassed by evacuating it with vacuum for 60 minutes. While the reaction vessel was being evacuated, the monomer solution consisting of 0.25 M MEDSAH (Sigma Aldrich) was dissolved in a solvent mixture of deionized water and ethanol (4:1). The solution was degassed for 40 min. using an argon purge. Once the reaction vessel and solvent were degassed, the monomer solution was transferred to the reaction vessel and heated to 68-70° C. While the reaction vessel was being heated up, TCPS dishes (BD Biosciences) were activated by UV ozone treatment (Jetlight Inc.) for 40 min. in order to create initiation sites on the surface. Surrogates consisting of poly(para-xylylene) coated silicon wafers and gold wafers were also added along with the cell culture dishes in order to enable thickness and contact angle measurement. After activation, the dishes were transferred to the reaction vessel and the temperature was raised to 76-80° C. Surface-initiated polymerization occurred over 2.5 hours under argon atmosphere at 76-80° C. Once the process was complete, TCPS plates and surrogates were removed from the reaction vessel and rinsed in a 1% saline solution at 50° C. overnight.

Atom Transfer Radical Polymerization

Poly[2-(methacryloyloxy)ethyl dimethyl-(3-sulfopropyl) ammonium hydroxide] (PMEDSAH) (Monomoer Polymer Dajac Labs, Trevose, Pa.) was polymerized using a typical ATRP procedure using Schlenk flask techniques. Initiator coated substrates were prepared according to the CVD process described above. Initiator-coated samples and uncoated TCPS were placed in a glove bag and degassed using 3 cycles of vacuum-argon purge. They were left at room temperature under argon. A mixture of methanol and water (4:1) was degassed by three cycles of freeze-pump-thaw. A small portion, (~20% v:v) of the degassed solvent was transferred to a degassed flask. The monomer was then dissolved in the main flask and the copper/ligand mixture was dissolved in the second flask. After 10 minutes the catalyst mixture was added to the monomer solution and mixed thoroughly at room temperature. The polymerization solution was finally transferred to the glove bag and distributed among the TCPS and the surrogates so that each substrate was submerged completely. The ATRP reaction was allowed to proceed for 1, 12, and 24 hours under argon atmosphere. After ATRP, surrogates and TCPS plates were rinsed with 1% sodium chloride solution and deionized water and dried. Residual copper, if any, was removed from the ATRP-modified surfaces by washing alternately with 5 mM Ethylenediamine tetracetic acid (EDTA) and 5 mM Calcium chloride solutions and finally rinsed with deionized water.

Contact Angle Measurement

Static contact angles of deionized water was measured using a contact angle goniometer. Measurements were taken at three different locations and averaged.

Streaming Potential Measurement

Polymer coatings were prepared directly on polystyrene slides in order to measure surface charge. An electrokinetic analyser SurPASS (Anton Paar GmBH) was used in clamping cell mode to acquire zeta potential values of the samples across a pH range of 3-10. Two titrations were performed for each sample, one proceeding from the neutral to the acidic range and another from the neutral to the basic range. 0.1 M Hydrochloric acid and 0.1M Sodium Hydroxide were used as titrants. 0.001 M Potassium Chloride was used as the electrolyte. pH changes were performed using an automated titration unit with pH being altered in steps of 0.3 with continuous stirring of the electrolyte solution. Streaming current was measured using Ag/AgCl electrodes and the helmohltz smoluchwski equation was sued to compute zeta potential. Flow rates of 50-70 ml/minute were used at a pressure of 400 mbar and a gap of 100 microns between the sample and the Polypropylene reference standard. Samples were rinsed for 3 minutes in between measurements at different pH points.

Atomic Force Microscopy (AFM)

The surface roughness of the PMEDSAH coatings was evaluated via atomic force microscopy (AFM) using a Dimension Icon (Bruker, Madison, Wis.). Measurements were taken in tapping mode at room temperature in air using NSC15 cantilevers (MikroMasch, San Jose, Calif.) with resonant frequency and spring constants of 20-75 N/m and 265-400 kHz respectively as probe tips. Measurements were taken at 1 Hz scan rate on a 2×2 micron area. Roughness values in the form of root mean square roughness ($R_a$) were acquired through a statistical analysis performed by the software by averaging over the scan region. Three values were acquired for each sample and averaged.

Preparation of Matrigel-Coated Substrates

Matrigel (BD BioSciences, San Jose, Calif., cat. no. 354277) was diluted to a concentration of 0.1 mg/ml in cold Dulbecco's modified Eagle's medium/F12 (DMEM/F12; GIBCO, Carlsbad, Calif., cat. no. 11330) and then applied to tissue culture polystyrene (TCPS) dishes (tissue culture-treated polystyrene; 35 mm; BD Falcon, cat. no. 353001). The coating was allowed to polymerize during 2 h incubation at room temperature. Before plating cells, excess Matrigel-DMEM/F12 solution was aspirated and the dishes were washed with sterilized Dulbecco's phosphate buffered saline (D-PBS, GIBCO, cat. no. 14190).

Cell Culture of hES Cells hESCs (H9 and H1, WiCell Research Institute, Madison, Wis.; CHB10, Children's Hospital Corporation, Boston, Mass.) were cultured on PMEDSAH with Human-Cell-Conditioned Medium (HCCM, Global Stem, Rockville, Md.) supplemented with 5 ng/mL of human recombinant basic fibroblast growth factor (bFGF; Invitrogen™, Grand Island, N.Y., cat. no. 13256-029). Differentiated cells were mechanically removed using a sterile pulled-glass pipet under a stereomicroscope (LeicaMZ9.5, Leica Microsystems Inc., Buffalo Grove, Ill.). Undifferentiated colonies were cut and collected as small cell clusters into a 1.5 mL centrifuge tube. After centrifugation and brief washing with PBS, cells were treated with 0.5 mL 0.25% Trypsin-EDTA (GIBCO, cat. no. 25200) at 37° C. The trypsinization was terminated by the addition of 1 ml human conditioned culture medium (HCCM) and brief centrifugation. The cell pellet was dispersed in HCCM supplemented with 5 ng/mL bFGF and 10 µM of ROCK inhibitor (Y27632, Sigma) and passed through a 40 µm nylon mesh cell strainer (BD Biosciences, Bedford, Mass.) to remove large cell aggregates. Single hESCs were counted and 20,000 cells were plated and cultured for 7 days. Matrigel, PMEDSAH and three types of ATRP PMEDSAH (25 nm, 105 nm and 176 nm) were compared in coated-dishes. The culture medium was replaced every other day. Single hESCs were passed once a week for 5 weeks using the same method but without removing the differentiated colonies before passage.

Alkaline Phosphatase Assay

An Alkaline Phosphatase Detection Kit (Millipore, Billerica, Mass., Cat. No. SCR004) was used for phenotypic assessment of ESC. Briefly, on day 7, cells were fixed with 4% paraformaldehyde in PBS for 1-2 minutes, then rinsed and incubated in the stain solution in the dark at room temperature for 15 minutes. The cells were rinsed and covered with 1×PBS to prevent drying prior to quantitative analysis. Undifferentiated colonies were identified by specific alkaline phosphatase staining.

Quantitative analysis of undifferentiated colony formation and the total cell number ImageJ software was used to count the number and area of undifferentiated colonies stained by alkaline phosphatase. The total number of cells grown on each dish was counted once per week from 1 to 5 weeks with hemocytometer. The total cell number of hESCs cultured on different substrates was converted to a calculated cell total assuming that all the cells were passed each week instead of 20,000 single cells. The theoretical yield of cells was determined with the formula $CN_{(n+1)}=CN_n \times TN_{(n+1)}/20000$, in which CN is the calculated total cell number, TN is the total cell number and n is the culture week.

Flow Cytometry Analysis hESCs cultured on different substrates from week 1 to 5 were washed with PBS and harvest by incubation in 0.25% trypsin-EDTA (GIBCO, cat. no. 25200). The trypsinization was terminated by adding 1 ml HCCM and the cells were incubated with human/Mouse SSEA-4 PE-conjugated antibody (R&D systems, Minneapolis, Minn. Cat no#: FAB1435P) and then analyzed by flow cytometry to determine the percentage of hESCs expressing SSEA-4. Analysis was carried out with MoFlo® Astrios™ (Beckman Coulter) using standard procedures. Background fluorescence and autofluorescence were determined using cells without treatment and incubated with Mouse IgG1 Phycoerythrin Isotype Control (R&D systems, Minneapolis, Minn. Cat no#: IC002P).

Immunofluorescence Staining

Cells grown on different substrates were fixed in 4% paraformaldehyde for 30 min at room temperature and then permeabilized with 0.1% Triton X-100 for 10 min. Primary antibodies raised against SSEA-4 (Santa Cruz Biotechnology, Santa Cruz, Calif., Cat. No. sc-21704), OCT3/4 (Santa Cruz Biotechnology, Santa Cruz, Calif., Cat. No. sc-8629), anti-SOX2 (Millipore, Billerica, Mass., Cat. No. AB5603), TRA-1-60 (Santa Cruz Biotechnology, Santa Cruz, Calif., Cat. No. sc-21705), TRA-1-81 (Millipore, Billerica, Mass., Cat. No. MAB4381), and NANOG (Abcam, Cambridge, Mass., Cat. No. ab80892) were diluted in 1% normal serum and incubated overnight at 4° C. and were detected with respective secondary antibodies. Sample images were captured using a Nikon TE2000-S inverted microscope with a Nikon DS-Ri1 camera.

RNA Isolation and Quantitative RT-PCR

Cells grown on different substrates were manually scraped from dishes and pelleted by centrifugation. RNA was isolated and purified using the RNeasy Mini-Kit (Qiagen, Valencia, Calif.) following the manufacturer's protocol. RNA quality and concentration was checked with a Synergy NEO HTS Multi-Mode Microplate Reader (BioTek Instruments, Winooski, Vt.). Reverse transcription from 1 ug of total RNA into cDNA was done using SuperScript™ III First-Strand Synthesis SuperMix (Invitrogen™, Grand Island, N.Y.). Quantitative PCR was performed using TaqMan probes (Applied Biosystems) and TaqMan Universal PCR Master Mix (Applied Biosystems) on 7900 HT Fast Real Time PCR system (Applied Biosystems). Gene expression data was normalized to the expression levels of GAPDH.

Analysis of hESC Pluripotency

Embryoid body (EB) formation and directed cell-lineage differentiation were performed to evaluate the pluripotency of hESCs grown on different substrates. EB formation was achieved by hESC clusters cultured in suspension in DMEM (Life Technologies, Grand Island, N.Y., Cat. No. 11965-092) supplemented with 10% FBS for 10 days to promote differentiation. Directed cell-lineage differentiation was performed on Matrigel using the following protocols (Yao et al., 2006). hESCs were induced to differentiate in chemically defined medium (CDM) base composed of DMEM/F12 (Invitrogen) supplemented with 1×N2 (Invitrogen), 1×B27 (Invitrogen), 0.11 mM 2-mercaptoethanol, 1 mM nonessential amino acids, 2 mM L-glutamine, and 0.5 mg/ml BSA (fraction V; Sigma Aldrich). To induce definitive endoderm (pancreatic differentiation), 100 ng/ml human recombinant activin A (STEMGENT) was added to CDM base and cells were cultured in this condition for 6 days, followed by culture in CDM base without activin A for an additional 9 days. For mesoderm (cardiomyocyte differentiation), cells were cultured in CDM base supplemented with 50 ng/ml human recombinant BMP4 (STEMGENT) and 50 ng/ml human recombinant activin A (STEMGENT) for 4 days, then further cultured in CDM base with no activin A and BMP4 for another 10 days. Forectoderm (neuronal differentiation), 100 ng/ml human recombinant Noggin (STEMGENT) was added to the CDM base and cells were cultured in this condition for 8 days.

Cytogenetic Evaluation

After 5 weeks of cell culture, standard G-band analysis on at least 20 cells was performed on cells cultured on 105 nm ATRP PMEDSAH by Cell Line Genetics (Madison, Wis.) using standard protocols.

Data Analysis

Data sets were compared using unpaired student t-test function in Excel (Microsoft, Seattle, Wash.) to calculate p values. Levels of statistical significance were set at $p<0.05$.

Results

Differences in Properties of PMEDSAH Coatings

PMEDSAH polymer coatings were fabricated using different surface-initiated polymerization procedures. One coating was prepared through UVO-initiated radical polymerization and three coatings were prepared using atom transfer radical polymerization conducted for different reaction times. Comparison of physicochemical properties between these four coatings was based on film thickness, wettability, surface roughness and zeta potential measurements. It was observed that films prepared through UVO-initiated polymerization did not exceed 35 nm in thickness and that molecular weight of the polymer could not be controlled. This may be attributed to the kinetics of conventional free radial polymerization where the radical lifetime is short and the termination step is quite rapid (Tang et al., 2008). In contrast, ATRP is capable forming thick and monodisperse PMEDSAH polymer films, when an appropriate catalyst quantity and reaction time is chosen. Due to the living nature of ATRP, it is capable of producing well-controlled reaction rates. Hence one can observe a gradual increase of film thickness from 25 nm in 1 hour to 176 nm in 24 hours.

The hydrophilicity of UVO-grafted PMEDSAH may be attributed to the affinity of water to the anionic sulphonate and cationic quaternary ammonium present in their side chains. The tendency of these functional groups to be hydrated leads to water penetration, swelling of the polymer brush and a lower contact angle. With ATRP however, the contact angle changed from 21.9° to 75.3° for films with thicknesses between about 25 and 176 nm. This transition from hydrophilic behavior to hydrophobic behavior was explained by Cheng et al. in terms of chain conformation and whether inter-chain or intra chain associations dominate.

Since neither grafting density nor molecular weight distribution can be controlled in the case of UVO-grafted films, the resulting polymer brush is likely to be dilute, polydisperse and unassociated. This means that ionic attractions between the sulphonate and the ammonium groups in the side chains are not dominant and that the polymer is fully hydrated resulting in a low contact angle. ATRP coatings, on the other hand, have a high and controllable grafting density resulting in greater proximity of polymer chains to each other and giving greater play to short range ionic interactions. While the present invention is not limited to any particular mechanism, and an understanding of the mechanism is not necessary to practice the invention, the following is believed. The 25 nm films would exhibit intra-chain associations resulting in a hydrophilic "mushroom regime" as they do not have sufficient number of ion-pairings to stretch out into a fully extended brush regime. 105 nm and 176 nm coatings, being of higher molecular weight, are able to form intermolecular chain associations. This de-swelling or collapse of the brush effectively seals out water as the ion-ion pairing prevents complete hydration of the ionic groups. As molecular weight increases, more ion pairs are created, increasing the strength o the association, extent of water exclusion and contact angle. These reduced ion-pairing effects between polymer side chains may also explain, why the UVO-grafted PMEDSAH exhibits a higher isoelectric point than the ATRP films even when the ATRP films are quite thick. Differences in the expression of surface charge of between ATRP and UVO films are due to systematic intra-chain and inter-chain associations in the former and none in the latter.

In several studies, engineering roughness into soft cell culture substrates in the form of nano-grooves and pillars has been shown to play a role in mediating cell adhesion (review by Ross et al, 2012). Hence, procedures were performed to quantify the roughness of the four coatings after performing a topographical examination using Atomic Force microscopy. It was observed that differences in roughness as measured by root-mean-square roughness values were not statistically significant between the four coatings.

Gel Architecture Influences the Formation of Undifferentiated hESCs Colonies

Figure 10:
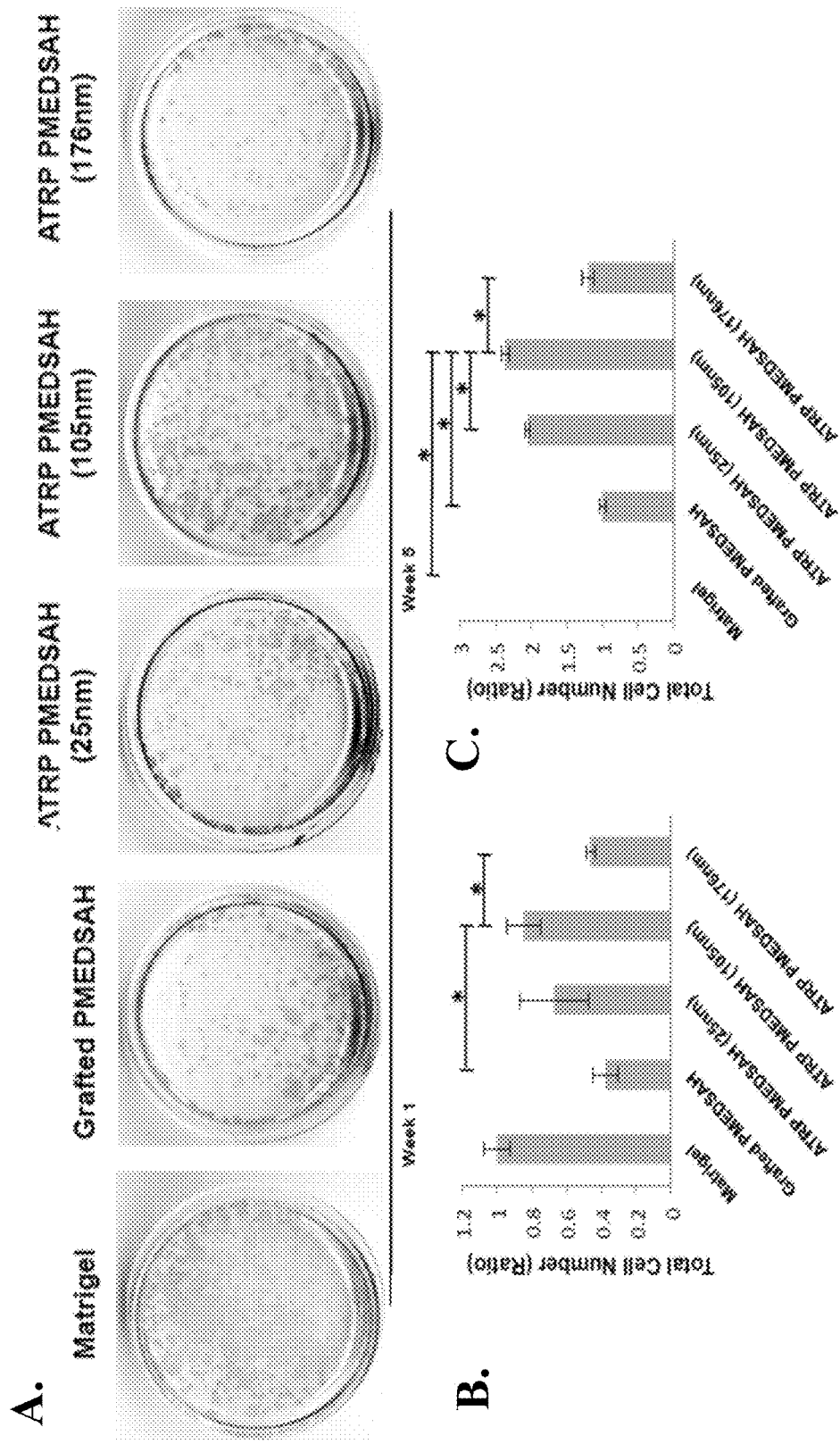
FIG. 10 shows results of culturing hESCs cells on Matrigel and various PMEDSAH membranes/films as described in Example 15.

Alkaline phosphatase activity was used to identify undifferentiated hESC colonies. When single CBH10 hESCs were cultured on ATRP PMEDSAH with a surface thickness of 105 nm, the number of undifferentiated colonies was similar to the Matrigel control group. However, compared to the other experimental groups, a significantly higher number of undifferentiated colonies were detected on the 105 nm thickness group (FIGS. 10a and 10b). No significant differences in colony surface areas were observed between experimental groups. Similar results were obtained with the H1hESC line, thus limiting the possibility of hES cell line-specific effects. Taken together, these results indicate that gel architecture influences colony formation of hESCs cultured on PMEDSAH.

Gel Architecture Influences the Expansion of hESCs

To quantify the impact of gel architecture on long-term expansion of hESCs, a consistent number (20,000) of single hESC scultured on Matrigel, PMEDSAH and ATRP PMEDSAH (25 nm, 105 nm, 176 nm) dishes were passed once a week a during 5 week experiment. Prior to each passage to new dishes, the total cell number was quantified and flow cytometry was performed on a subset of cells to evaluate the expression of SSEA-4, a hESC marker. The percentage of SSEA-4 positive cells ranged from 96.65% to 99.95% and was not statistically different among the different substrates. However, it was observed that the total number of cells that adhered to Matrigel decreased after each passage and cells on Matrigel would not survive after 4 passages. In contrast, single hESCs cultured on ATRP PMEDSAH continued to thrive with each passage. hESC growth was particularly robust on the ATRP PMEDSAH with a 105 nm surface thickness, which supported a higher total cell number than the other experimental groups (FIG. 10c).

The hESC cell number that would theoretically be achieved after 5 passages if the total number of cells were passed each week instead of only 20,000 cells was calculated for each substrate. The theoretical yield of cells was determined with the formula $CN_{(n+1)}=CN_n \times TN_{(n+1)}/20000$, in which CN is the calculated total cell number, TN is the total cell number and n is the culture week. Using this formula, it was estimated that 105 nm ATRP PMEDSAH could expand to $4.8 \times 10^9$ hESCs in 5 weeks. This compares to 20,000 cells used for the original plating. This level of hESC expansion on ATRP PMEDSAH (105 nm) is 33.6-, 1.6- and 12.7-fold greater than for the grafted PMEDSAH, 25 nm and 176 nm ATRP PMEDSAH, respectively. These calculated total cell numbers clearly demonstrated that gel architecture influences hESCs expansion after multiple passages.

Modified PMEDSAH Supports hESC Stemness, Pluripotency and Genomic Stability

Quantitative RT-PCR analysis of cells after 5 passages showed that the expression levels of hESC markers OCT4, SOX2, KLF4 and NANOG were similar among hESCs cultured on grafted PMEDSAH and ATRP PMEDSAH (25 nm, 105 nm, 176 nm). Immunofluorescent staining of OCT4 and SSEA-4 in hESCs was also strong when cultured on both grafted PMEDSAH and ATRP PMEDSAH (25 nm, 105 nm and 176 nm) dishes. Because 105 nm ATRP PMEDSAH demonstrated a stronger capacity to support hESC self-renewal and expansion, an additional hESC line was also cultured on 105 nm ATRP PMEDSAH during the same period of time. In addition to OCT4 and SSEA-4, primary antibodies to SOX2, TRA-1-60, NANOG and TRA-1-81 were used for immunofluorescence staining of H1 hESCs. H1h ESCs were positive for all these hESC markers on 105 nm ATRP PMEDSAH.

The pluripotency of the hESCs cultured on 105 nm ATRP PMEDSAH was determined by the ability of the polymer to support EB formation and directed cell-lineage differentiation after 5 passages. The hESC clusters cultured in suspension formed EBs and expressed genes representing the three germ layers: endoderm, mesoderm and ectoderm. Furthermore, specific cell-lineage differentiation was successfully directed and representative genes were expressed from cells representative of each germ layer. For endoderm differentiation, treatment with activin A resulted in higher RNA levels of FOXA2, SOX17, PDX1 and AFP. For mesoderm induction, the combination of activin A and BMP4 treatment led to up-regulation of TNN13, NKX2-5 and HESX1. For ectoderm differentiation, which was in response to treatment of Noggin, RNA levels for NES, SOX1, NEUROD1 and PAX6 were significantly increased. Taken together, these results demonstrate that ATR PPMEDSAH with a 105 nm surface thickness supports the pluripotency of hESCs, by which the cells were able to differentiate into derivatives of the three germ layers in chemically defined conditions.

Because hESC chromosomal changes may occur during long-term culture (Baker et al., 2007), the genetic stability of hESCs on 105 nm ATRP PMEDSAH was evaluated by Standard G-band analysis after 5 passages. The results demonstrated a normal human male karyotype.

In summary, all these evidence indicated that hESCs maintained on ATRP PMEDSAH with a 105 nm surface thickness retained their characteristics such as stemness, pluripotency and genomic stability during long-term culture.

Discussion

The evolution of hESC culture from feeder-cell dependence and non-defined conditions to feeder-free and defined microenvironments has been accompanied by the development of new culture materials. To reduce the instability and potential contamination due to feeder cells, xenogenic culture systems, such as Matrigel™ and human recombinant proteins, such as laminin have been applied (Xu et al., 2001; Braam et al., 2008; Miyazaki et al., 2008; Nagaoka et al., 2010). Subsequently, fully synthetic substrates have been developed (Li et al., 2006; Derda et al., 2007; Brafman et al., 2010; Klim et al., 2010; Kolhar et al., 2010; Mei et al., 2010; Melkoumian et al., 2010; Villa-Diaz et al., 2010; Irwin et al., 2011). As a fully defined synthetic substrate, PMEDSAH is very promising because of strong capacity to support hESC growth with chemically-defined and xenogeneic-free medium.

Cell adhesion and expansion are much higher on the 105 nm and 25 nm thick PMEDSAH coatings compared to the 176 nm thick coating or the UVO-grafted PMEDSAH. Gel architecture can influence protein-polymer interactions and results in differences in protein adsorption. If the proteins bind to the interior of the polymer chains or to the substrate rather than to the interface, it will result in a lower number of proteins available at the surface to bind to cells. While the present invention is not limited to any particular mechanism, this is the likely mode of adsorption for the UVO-grafted brush because of the low osmotic penalty of protein penetration into the polymer chains. The combined effects of high thickness and strong intermolecular chain attraction would make it difficult for the protein molecules to overcome the osmotic penalty of insertion. This results in a high surface density of proteins that mediate cell adhesion and result in higher efficiency of the 105 nm thick coating.

Since Matrigel is the first and current most commonly used feeder-free substrate for hESC culture, it was used as control group in this Example. Interestingly, it was found that the number of hESCs grown on Matrigel decreased after each passage due to fewer cell adhesions. Meanwhile, grafted and ATRP PMEDSAH can both support hESC expansion in long-term culture. Particularly ATRP PMEDSAH with a 105 nm surface thickness led to a higher total cell number compared to all the other experimental groups. In addition, the hESCs retained their pluripotency and karyotype after multiple passages during long-term culture, which indicated that the hESCs maintained their characteristics and genetic stability. By modifying the surface thickness of the PMEDSAH, the gel architecture of PMEDSAH was altered. In addition to significantly higher efficiency in hESC expansion during long-term culture, PMADSAH (grafted and ATRP) has the following advantages compared to Matrigel: defined, more stable, show minimal lot-to-lot variability, easily prepared and compatible with standard sterilization techniques. All of these make 105 nm thick ATRP PMEDSAH a very good stem cell culture polymer and ATRP a superior polymer fabrication method for increasing the effectiveness of clinical grade hESC expansion during long-term culture.

REFERENCES

All of the references below are herein incorporated by reference.

Baker et al. (2007). Nat Biotechnol 25: 207-215.
Braam et al. (2008). Stem Cells 26: 2257-2265.
Brafman et al. (2010). Biomaterials 31: 9135-9144.
Derda et al. (2007). ACS Chem Biol 2: 347-355.
Irwin et al. (2011). Biomaterials 32: 6912-6919.
Klim et al. (2010). Nat Methods 7: 989-994.
Kolhar et al. (2010). J Biotechnol 146: 143-146.
Li et al. (2006). J Biomedical Mater Res A 79: 1-5.
Mei et al. (2010). Nat Mater 9: 768-778.
Melkoumian et al. (2010). Nat Biotechnol 28: 606-610.
Miyazaki et al. (2008). Biochem Biophys Res Commun 375: 27-32.
Nagaoka et al. (2010). BMC Dev Biol 10: 60.
Richards et al. (2003). Stem Cells 21: 546-556.
Thomson et al. (1998). Science 282: 1145-1147.
Villa-Diaz et al. (2010). Nat Biotechnol 28: 581-583.
Villa-Diaz et al. (2013). Stem Cells 31: 1-7.
Wang and Matyjaszewski (1995). Macromolecules 28: 7901-7910.
Xu et al. (2001). Nat Biotechnol 19: 971-974.
Yao S, et al. (2006). Proc Natl Acad Sci USA 103: 6907-6912.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition for growth and maintenance of cells or embryonic tissue comprising:
   a) a synthetic polymer matrix comprising poly[2-(methacryloyloxy)ethyl dimethyl-(3-sulfopropyl)ammonium hydroxide] (PMEDSAH), and
   b) a culture medium.

2. A kit or system comprising:
   a) a synthetic polymer matrix, wherein said synthetic polymer matrix comprises poly[2-(methacryloyloxy)ethyl dimethyl-(3-sulfopropyl)ammonium hydroxide] (PMEDSAH), and
   b) culture medium.

* * * * *